United States Patent
De La Rama et al.

(10) Patent No.: US 8,979,839 B2
(45) Date of Patent: Mar. 17, 2015

(54) ASSEMBLY OF STAGGERED ABLATION ELEMENTS

(75) Inventors: Alan De La Rama, Cerritos, CA (US); Cary Hata, Irvine, CA (US)

(73) Assignee: St. Jude Medical, Inc., St. Paul, MN (US)

( * ) Notice: Subject to any disclaimer, the term of this patent is extended or adjusted under 35 U.S.C. 154(b) by 1158 days.

(21) Appl. No.: 12/945,982

(22) Filed: Nov. 15, 2010

(65) Prior Publication Data

US 2011/0118726 A1 May 19, 2011

Related U.S. Application Data

(60) Provisional application No. 61/260,978, filed on Nov. 13, 2009.

(51) Int. Cl.
*A61B 18/14* (2006.01)
*A61B 17/00* (2006.01)
(Continued)

(52) U.S. Cl.
CPC ... *A61B 18/1492* (2013.01); *A61B 2017/00867* (2013.01); *A61B 2018/00011* (2013.01);
(Continued)

(58) Field of Classification Search
CPC ........ A61B 18/04; A61B 18/12; A61B 18/14; A61B 18/148; A61B 18/1402; A61B 18/1442; A61B 18/1445; A61B 18/1477; A61B 18/1492; A61B 18/18; A61B 18/082; A61B 2018/00214; A61B 2018/00267; A61B 2018/14; A61B 2018/1405; A61B 2018/1407; A61B 2018/1467; A61B 2018/1475; A61B 2018/141; A61B 5/6858
USPC .............. 606/33, 34, 41, 42, 47–50; 600/374, 600/381
See application file for complete search history.

(56) References Cited

U.S. PATENT DOCUMENTS 3,650,277 A   3/1972   Sjostrand et al.
4,658,819 A   4/1987   Harris et al.
(Continued)

FOREIGN PATENT DOCUMENTS

WO   94/22366 A1   10/1994
WO   97/45157      12/1997
(Continued)

OTHER PUBLICATIONS

Abboud, Francois M., The Sympathetic System in Hypertension, State-of-the-Art Review, Hypertension Journal of the American Heart Association, Hypertension 4 (suppl II): II-208-II-225, 1982.
(Continued)

*Primary Examiner* — Michael Peffley
*Assistant Examiner* — Khadijeh Vahdat
(74) *Attorney, Agent, or Firm* — Armstrong Teasdale LLP

(57) ABSTRACT

An ablation catheter comprises a catheter body extending longitudinally between a proximal end and a distal end along a longitudinal axis; and an ablation element assembly comprising ablation elements connected to the catheter body, each ablation element to be energized to produce an ablation zone. The ablation elements are distributed in a staggered configuration such that the ablation zones of the ablation elements span one or more open arc segments around the longitudinal axis, but the ablation zones of all ablation elements projected longitudinally onto any lateral plane which is perpendicular to the longitudinal axis span a substantially closed loop around the longitudinal axis. Since the ablation zones do not form a closed loop, the risk of renal artery/vein stenosis is reduced or eliminated. Since the ablation zones of all ablation elements projected longitudinally onto any lateral plane span a substantially closed loop, substantially complete renal denervation is achieved.

8 Claims, 9 Drawing Sheets

(51) Int. Cl.
*A61B 18/00* (2006.01)
*A61B 18/12* (2006.01)

(52) U.S. Cl.
CPC .............. *A61B2018/0016* (2013.01); *A61B 2018/00214* (2013.01); *A61B 2018/00267* (2013.01); *A61B 2018/00654* (2013.01); *A61B 2018/00797* (2013.01); *A61B 2018/124* (2013.01); *A61B 2018/1467* (2013.01); *A61B 2018/1475* (2013.01); *A61B 2018/1497* (2013.01); *A61B 2218/002* (2013.01); *C08L 2201/12* (2013.01); *A61B 2018/00404* (2013.01); *A61B 2018/00434* (2013.01); *A61B 2018/00511* (2013.01)
USPC ................................................. 606/41

(56) References Cited

U.S. PATENT DOCUMENTS

| | | | |
|---|---|---|---|
| 5,035,694 A | 7/1991 | Kasprzyk et al. |
| 5,255,679 A | 10/1993 | Imran |
| 5,300,068 A | 4/1994 | Rosar et al. |
| 5,368,591 A | 11/1994 | Lennox et al. |
| 5,387,233 A | 2/1995 | Alferness et al. |
| 5,465,717 A | 11/1995 | Imran et al. |
| 5,531,779 A | 7/1996 | Dahl et al. |
| 5,598,848 A | 2/1997 | Swanson et al. |
| 5,607,462 A | 3/1997 | Imran |
| 5,628,313 A | 5/1997 | Webster, Jr. |
| 5,676,662 A | 10/1997 | Fleischhacker et al. |
| 5,707,400 A | 1/1998 | Terry, Jr. et al. |
| 5,769,077 A | 6/1998 | Lindegren |
| 5,772,590 A | 6/1998 | Webster, Jr. |
| 5,893,885 A | 4/1999 | Webster, Jr. |
| 5,897,553 A | 4/1999 | Mulier et al. |
| 5,954,649 A | 9/1999 | Chia et al. |
| 5,954,719 A | 9/1999 | Chen et al. |
| 6,004,269 A | 12/1999 | Crowley et al. |
| 6,012,457 A | 1/2000 | Lesh |
| 6,016,437 A | 1/2000 | Tu et al. |
| 6,024,740 A | 2/2000 | Lesh et al. |
| 6,073,048 A | 6/2000 | Kieval et al. |
| 6,096,037 A | 8/2000 | Mulier et al. |
| 6,117,101 A | 9/2000 | Diederich et al. |
| 6,161,543 A | 12/2000 | Cox et al. |
| 6,178,349 B1 | 1/2001 | Kieval |
| 6,200,312 B1 | 3/2001 | Zikorus et al. |
| 6,216,044 B1 | 4/2001 | Kordis |
| 6,233,491 B1 | 5/2001 | Kordis et al. |
| 6,283,951 B1 | 9/2001 | Flaherty et al. |
| 6,287,608 B1 | 9/2001 | Levin et al. |
| 6,292,695 B1 | 9/2001 | Webster, Jr. et al. |
| 6,322,559 B1 | 11/2001 | Daulton et al. |
| 6,460,545 B2 | 10/2002 | Kordis |
| 6,522,926 B1 | 2/2003 | Kieval et al. |
| 6,613,045 B1 | 9/2003 | Laufer et al. |
| 6,616,624 B1 | 9/2003 | Kieval |
| 6,635,054 B2 | 10/2003 | Fjield et al. |
| 6,656,174 B1 | 12/2003 | Hegde et al. |
| 6,669,655 B1 | 12/2003 | Acker et al. |
| 6,699,231 B1 | 3/2004 | Sterman et al. |
| 6,748,255 B2 | 6/2004 | Fuimaono et al. |
| 6,805,131 B2 | 10/2004 | Kordis |
| 6,845,267 B2 | 1/2005 | Harrison et al. |
| 6,954,977 B2 | 10/2005 | Maguire et al. |
| 6,970,730 B2 | 11/2005 | Fuimaono et al. |
| 7,122,031 B2 | 10/2006 | Edwards et al. |
| 7,149,574 B2 | 12/2006 | Yun et al. |
| 7,155,284 B1 | 12/2006 | Whitehurst et al. |
| 7,162,303 B2 | 1/2007 | Levin et al. |
| 7,245,955 B2 | 7/2007 | Rashidi |
| 7,291,146 B2 | 11/2007 | Steinke et al. |
| 7,363,076 B2 | 4/2008 | Yun et al. |
| 7,419,486 B2 | 9/2008 | Kampa |
| 7,465,288 B2 | 12/2008 | Dudney et al. |
| 7,468,062 B2 | 12/2008 | Oral et al. |
| 7,481,803 B2 | 1/2009 | Kesten et al. |
| 7,653,438 B2 | 1/2010 | Deem et al. |
| 7,717,948 B2 | 5/2010 | Demarais et al. |
| 7,742,795 B2 | 6/2010 | Stone et al. |
| 7,850,685 B2 | 12/2010 | Kunis et al. |
| 7,949,407 B2 | 5/2011 | Kaplan et al. |
| 8,145,316 B2 | 3/2012 | Deem et al. |
| 8,224,416 B2 | 7/2012 | de la Rama et al. |
| 8,343,213 B2 | 1/2013 | Salahieh et al. |
| 8,347,891 B2 | 1/2013 | Demarais et al. |
| 8,442,639 B2 | 5/2013 | Walker et al. |
| 8,454,594 B2 | 6/2013 | Demarais et al. |
| 8,545,495 B2 | 10/2013 | Scheib |
| 2002/0068885 A1 | 6/2002 | Harhen et al. |
| 2002/0120304 A1 | 8/2002 | Mest |
| 2003/0050681 A1 | 3/2003 | Pianca et al. |
| 2003/0060858 A1 | 3/2003 | Kieval et al. |
| 2003/0074039 A1 | 4/2003 | Puskas |
| 2003/0114739 A1 | 6/2003 | Fuimaono et al. |
| 2003/0216792 A1 | 11/2003 | Levin et al. |
| 2003/0233099 A1 | 12/2003 | Danaek et al. |
| 2004/0215186 A1 | 10/2004 | Cornelius et al. |
| 2005/0096647 A1 | 5/2005 | Steinke et al. |
| 2005/0159742 A1* | 7/2005 | Lesh .............................. 606/41 |
| 2005/0288730 A1 | 12/2005 | Deem et al. |
| 2006/0089678 A1 | 4/2006 | Shalev |
| 2007/0135875 A1 | 6/2007 | Demarais et al. |
| 2008/0125772 A1 | 5/2008 | Stone et al. |
| 2008/0255478 A1 | 10/2008 | Burdette |
| 2009/0076409 A1 | 3/2009 | Wu et al. |
| 2010/0016762 A1 | 1/2010 | Thapliyal et al. |
| 2010/0094209 A1 | 4/2010 | Drasler et al. |
| 2010/0168737 A1 | 7/2010 | Grunewald |
| 2010/0249773 A1 | 9/2010 | Clark et al. |
| 2010/0268307 A1 | 10/2010 | Demarais et al. |
| 2010/0286684 A1 | 11/2010 | Hata et al. |
| 2011/0004087 A1 | 1/2011 | Fish et al. |
| 2011/0118726 A1 | 5/2011 | de la Rama et al. |
| 2011/0137298 A1 | 6/2011 | Nguyen et al. |
| 2011/0160720 A1 | 6/2011 | Johnson |
| 2011/0213231 A1 | 9/2011 | Hall et al. |
| 2011/0257641 A1 | 10/2011 | Hastings et al. |
| 2011/0264011 A1 | 10/2011 | Wu et al. |
| 2011/0264086 A1 | 10/2011 | Ingle |
| 2012/0143097 A1 | 6/2012 | Pike, Jr. |
| 2012/0143298 A1 | 6/2012 | Just et al. |
| 2012/0296232 A1 | 11/2012 | Ng |
| 2012/0323233 A1 | 12/2012 | Maguire et al. |
| 2013/0116737 A1 | 5/2013 | Edwards et al. |
| 2013/0131743 A1 | 5/2013 | Yamasaki et al. |
| 2013/0144251 A1 | 6/2013 | Sobotka |
| 2013/0172715 A1 | 7/2013 | Just et al. |

FOREIGN PATENT DOCUMENTS

| | | |
|---|---|---|
| WO | 00/66020 | 11/2000 |
| WO | 01/00273 | 1/2001 |
| WO | 01/22897 | 4/2001 |
| WO | 02/26314 | 4/2002 |
| WO | 03/082080 | 10/2003 |
| WO | 2006/041881 | 4/2006 |
| WO | 2007/149970 | 12/2007 |
| WO | 2008/141150 | 11/2008 |
| WO | 2008/151001 | 12/2008 |
| WO | 2012/064818 | 5/2012 |
| WO | 2012/106492 | 8/2012 |

OTHER PUBLICATIONS

Allen, Edgar V., Sympathectomy for Essential Hypertension, Circulation Journal of the American Heart Association, vol. VI, Jul. 1952, 131-140.

Anderson, Erling A. et al, Elevated Sympathetic Nerve Activity in Borderline Hypertensive Humans, Evidence From Direct Intraneural Recordings, Hypertension Journal of the American Heart Association, vol. 14, No. 2, Aug. 1989, 177-183.

(56) References Cited

OTHER PUBLICATIONS

Ardian, Inc., Ardian(R) Receives 2010 EuroPCR Innovation Award and Demonstrates Further Durability of Renal Denervation Treatment for Hypertension, PR Newswire, Jun. 3, 2010.
Arentz, Thomas et al, Feasibility and Safety of Pulmonary Vein Isolation Using a New Mapping and Navigation System in Patients with Refractory Atrial Fibrillation, Circulation Journal of the American Heart Association, Nov. 18, 2003, 2484-2490.
Badoer, Emilio et al, Cardiac Afferents Play the Dominant Role in Renal Nerve Inhibition Elicited by Volume Expansion in the Rabbit, American Journal of Physiology, 1998, R383-R388.
Bakris, George L. et al, Baroreflex Activation Therapy Provides Durable Benefit in Patients with Resistant Hypertension: Results of Long-Term Follow-up in the Rheos Pivotal Trial, J Am Soc Hypertens. Mar.-Apr. 2012;6 (2):152-8.
Bao, Gang et al, Blood Pressure Response to Chronic Episodic Hypoxia: Role of the Sympathetic Nervous System, American Journal of Physiology, 1997, 95-101.
Barajas, Luciano et al, Anatomy of the Renal Innervation: Intrarenal Aspects and Ganglia of Origin, Canadian Journal of Physiology and Pharmacology, vol. 70, No. 5, May 1992, 735-749.
Barajas, Luciano et al, Monoaminergic Innervation of the Rat Kidney: A Quantitative Study, American Journal of Physiology, vol. 259, No. 3, Sep. 1990, F503-F511.
Bardram, Linda et al, Late Results After Surgical Treatment of Renovascular Hypertension, A Follow-up Study of 122 Patients 2-18 Years After Surgery, Annals of Surgery, vol. 201, No. 2, Feb. 1985, 219-224.
Bello-Reuss, Elsa et al, Effect of Renal Sympathetic Nerve Stimulation on Proximal Water and Sodium Reabsorption, The Journal of Clinical Investigation, vol. 57, Apr. 1976, 1104-1107.
Bello-Reuss, Elsa et al, Effects of Acute Unilateral Renal Denervation in the Rat, The Journal of Clinical Investigation, vol. 56, Jul. 1975, 208-217.
Benito, Fernando et al, Radiofrequency Catheter Ablation of Accessory Pathways in Infants, Heart, 1997, 78, 160-162.
Bernardi, Luciano et al, Influence of Type of Surgery on the Occurrence of Parasympathetic Reinnervation After Cardiac Transplantation, Circulation Journal of The American Heart Association, Apr. 14, 1998;97(14):1368-74.
Bertog, Stefan C. et al, Renal Denervation for Hypertension, JACC: Cardiovascular Interventions, vol. 5, No. 3, Mar. 2012, 249-258.
Bertram, Harald et al, Coronary Artery Stenosis After Radiofrequency Catheter Ablation of Accessory Atrioventricular Pathways in Children with Ebstein's Malformation, Circulation Journal of the American Heart Association, 2001, 538-543
Blankestijn, Peter J. et al, Renal Denervation: Potential Impact on Hypertension in Kidney Disease?, Nephrol Dial Transplant (2011) 0: 1-3.
Blankestijn, Peter J. et al, Sympathetic Overactivity in Renal Failure Controlled by ACE Inhibition: Clinical Significance, Nephrol Dial Transplant, 2000, 15, 755-758.
Blum, Ulrich et al, Treatment of Ostial Renal-Artery Stenoses with Vascular Endoprostheses After Unsuccessful Balloon Angioplasty, The New England Journal of Medicine, vol. 336, No. 7, Feb. 1997, 459-465
Brinkmann, Julia et al, Catheter-Based Renal Nerve Ablation and Centrally Generated Sympathetic Activity in Difficult-to-Control Hypertensive Patients Prospective Case Series, Hypertension. 2012;60:1485-1490.
Brookes, Linda et al, Renal Denervation: Is Reality Meeting Expectations?, An Interview with Michel Azizi, MD, PhD, Medscape, Jan. 7, 2013.
Bunte, Matthew C. et al, Endovascular Treatment of Resistant and Uncontrolled Hypertension, JACC: Cardiovascular Interventions, vol. 6, No. 1, 2013, 1-9.
Calleary, Hickey D. et al, Pre-Transplant Bilateral Native Nephrectomy for Medically Refractory Hypertension, The Irish Medical Journal, Jul.-Aug. 2001;94(7):214-6

Callens, David J. et al, Narrowing of the Superior Vena Cava-Right Atrium Junction During Radiofrequency Catheter Ablation for Inappropriate Sinus Tachycardia: Analysis with Intracardiac Echocardiography, Journal of the American College of Cardiology, vol. 33, No. 6, 1999, 1667-1670.
Campese, V.M., Is Hypertension in Chronic Renal Failure Neurogenic in Nature?, Nephrol Dial Transplant, 1994, 9: 741-742.
Campese, Vito M. et al, Neurogenic Factors in Renal Hypertension, Current Hypertension Reports, 2002 4: 256-260.
Campese, Vito M. et al, Renal Afferent Denervation Prevents Hypertension in Rats With Chronic Renal Failure, Hypertension, 1995, 25, 878-882.
Campese, Vito M. et al, Renal Afferent Denervation Prevents the Progression of Renal Disease in the Renal Ablation Model of Chronic Renal Failure in Rat, American Journal of Kidney Disease, vol. 26, No. 5, Nov. 1995, 861-865.
Campese, Vito M., Interventional Hypertension: A New Hope or a New Hype? The Need to Redefine Resistant Hypertension, J Hypertens. Nov. 2013;31(11):2118-21.
Canadian Agency for Drugs and Technologies in Health, Catheter-Based Renal Denervation for Treatment-Resistant Hypertension; Issues in Emerging Health Technologies, Issue 121, Mar. 2013.
Carlstedt, Thomas et al, Regrowth of Lesioned Dorsal Root Nerve Fibers into the Spinal Cord of Neonatal Rats, Neuroscience Letters Feb. 10, 1987;74(1):14-8.
Chabanier, H. et al, On the Decapsulation and Neurectomy of the Kidnesy in Permanent Hypertensive States, The Medical Press, Feb. 22, 1936, No. 16, 307-310.
Ciccone, C D et al, Effects of Acute Renal Denervation on Kidney Function in Deoxycorticosterone Acetate-Hypertensive Swine, Hypertension Journal of the American Heart Association, Oct. 1986, vol. 8, No. 10, 925-931.
Ciriello, John et al, Renal Afferents and Hypertension, Current Hypertension Reports 2002, 4:136-142.
Converse, Richard L. et al, Sympathetic Overactivity in Patients with Chronic Renal Failure, The New England Journal of Medicine, vol. 327, No. 27, 1992, 1912-1918.
Crile, George, The Clinical Results of Celiac Ganglionectomy in the Treatment of Essential Hypertension, Annals of Surgery, Jun. 1938; 107(6): 909-916.
Cruickshank, J.M., Beta-Blockers Continue to Surprise Us, European Heart Journal (2000) 21, 354-364.
Curtis, John J. et al, Surgical Therapy for Persistent Hypertension After Renal Transplantation, Transplantation, vol. 31, No. 2, 1981, 125-128.
Dailey, U.G., Surgical Treatment of Hypertension: A Review-Part II, Journal of the National Medical Association, May 1948, vol. 40, No. 3., 113-116.
Dailey, U.G., Surgical Treatment of Hypertension: A Review-Part III, Journal of the National Medical Association, Jul. 1948, vol. 40, No. 4, 160-162.
Dailey, U.G., The Surgical Treatment of Hypertension: A Review, Journal of the National Medical Association, Mar. 1948, vol. 40, No. 2, 76-79.
Davis, Mark I. et al, Effectiveness of Renal Denervation Therapy for Resistant Hypertension a Systematic Review and Meta-Analysis, Journal of the American College of Cardiology, vol. 62, No. 3, 2013, 231-241.
De Wardener, H.E., The Hypothalamus and Hypertension, Physiological Reviews,vol. 81, No. 4, Oct. 2001.
Dequattro V. et al, The Sympathetic Nervous System: The Muse of Primary Hypertension, Journal of Human Hypertension, 2002, 16 (Suppl 1), S64-S69.
Dibona, Gerald F. et al, Neural Control of Renal Function, Physiological Reviews, vol. 77, No. 1, Jan. 1997, 75-197.
Dibona, Gerald F. et al, Translational Medicine: The Antihypertensive Effect of Renal Denervation, Americal Journal of Physiology, 2010, 298, R245-R253.
Dibona, Gerald F., Neural Control of Renal Function: Cardiovascular Implications, Hypertension Journal of The American Heart Association, vol. 13, No. 6, Part 1, Jun. 1989, 539-548.

(56) References Cited

OTHER PUBLICATIONS

Dibona, Gerald F., Neural Control of the Kidney: Functionally Specific Renal Sympathetic Nerve Fibers, American Journal of Physiology, 2000, 279, R1517-R1524.

Dibona, Gerald F., Neural Control of the Kidney: Past, Present, and Future, Hypertension Journal of the American Heart Association, vol. 41, Mar. 2003, Part II, 621-624.

Dibona, Gerald F., Renal Innervation and Denervation: Lessons from Renal Transplantation Reconsidered, Artificial Organs, vol. 11, No. 6, 1987, 457-462.

Dibona, Gerald F., Role of the Renal Nerves in Renal Sodium Retention and Edema Formation, Trans Am Clin Climatol Assoc. 1990; 101: 38-45.

Dibona, Gerald F., Sympathetic Nervous System and Hypertension, Hypertension Journal of The American Heart Association, 2013; 61: 556-560.

Dibona, Gerald F., Sympathetic Nervous System and the Kidney in Hypertension, Curr Opin Nephrol Hypertens. Mar. 2002;11(2):197-200.

Dibona, Gerald F., The Sympathetic Nervous System and Hypertension, Hypertension Journal of The American Heart Association, Vo. 43, Feb. 2004, 147-150.

Doumas, Michael et al, Interventional Management of Resistant Hypertension, The Lancet, vol. 373, Apr. 11, 2009, pp. 1228-1230.

Dubuc, Marc et al, Feasibility of Cardiac Cryoablation Using a Transvenous Steerable Electrode Catheter, Journal of Interventional Cardiac Electrophysiology, 1998, 2: 285-292.

Elmula, Fadl et al, Renal Sympathetic Denervation in Patients With Treatment-Resistant Hypertension After Witnessed Intake of Medication Before Qualifying Ambulatory Blood Pressure, Hypertension. 2013;62:526-532.

Esler, M. et al, Sympathetic Nerve Activity and Neurotransmitter Release in Humans: Translation from Pathophysiology into Clinical Practice, Scandinavian Physiological Society, 2003, 177, 275-284.

Esler, Murray D. et al, Renal Sympathetic Denervation in Patients with Treatment-Resistant Hypertension (The Symplicity HTN-2 Trial): A Randomised Controlled Trial, Lancet, 2010; 376:1903-1909.

Esler, Murray et al, Assessment of Human Sympathetic Nervous System Activity from Measurements of Norepinephrine Turnover, Hypertension Journal of the American Heart Association, vol. 11, No. 1, Jan. 1988, 3-20.

Evelyn, Kenneth A. et al, Effect of Thoracolumbar Sympathectomy on the Clinical Course of Primary (Essential) Hypertension, American Journal of Medicine, Feb. 1960, 188-221.

Freyberg, R. H. et al, The Effect on the Kidney of Bilateral Splanchnicectomy in Patients with Hypertension, The Journal of Clinical Investigation, vol. 16, Issue 1, Jan. 1937, 49-65.

Gafoor, Sameer et al, Nonresponders to Renal Denervation for Resistant Hypertension, Endovascular Today, Oct. 2013, 63-70.

Garel, L. et al, Fatal Outcome After Ethanol Renal Ablation in Child with End-Stage Kidneys; AJR 146:593-594, Mar. 1986.

Gazdar, A. F. et al, Neural Degeneration and Regeneration in Human Renal Transplants, The New England Journal of Medicine, vol. 238, No. 5, Jul. 1970, 222-224.

Goldberg, Michael R. et al, Reconstructive Vascular Surgery for Renovascular Hypertension, Can Med Assoc J. Feb. 2, 1974;110(3):275-80.

Golwyn, Daniel H. et al, Percutaneous Transcatheter Renal Ablation with Absolute Ethanol for Uncontrolled Hypertension or Nephrotic Syndrome: Results in 11 Patients with End-Stage Renal Disease, Journal of Vascular and Interventional Radiology, Jul.-Aug. 1997, vol. 8, No. 4, 527-533.

Gorisch, Wolfram et al, Heat-Induced Contraction of Blood Vessels, Lasers in Surgery and Medicine 2:1-13 (1982).

Grassi, Guido et al, Baroreflex Control of Sympathetic Nerve Activity in Essential and Secondary Hypertension, Hypertension Journal of The American Heart Association, 1998;31:68-72.

Grassi, Guido et al, Dissociation Between Muscle and Skin Sympathetic Nerve Activity in Essential Hypertension, Obesity, and Congestive Heart Failure, Hypertension. 1998;31:64-67.

Grimson, Keith S. et al, Results of Treatment of Patients with Hypertension by Total Thoracic and Partial to Total Lumbar Sympathectomy, Splanchnicectomy and Celiac Ganglionectomy, Annals of Surgery, Jun. 1949, vol. 129, No. 6, 850-871.

Grimson, Keith S. et al, Total Thoracic and Partial to Total Lumbar Sympathectomy, Splanchnicectomy and Celiac Ganglionectomy for Hypertension, Annals of Surgery, Oct. 1953, vol. 138, No. 4, 532-547.

Grimson, Keith S., Total Thoracic and Partial to Total Lumbar Sympathectomy and Celiac Ganglionectomy in the Treatment of Hypertension, Annals of Surgery, Oct. 1941, vol. 114, No. 4, 753-775.

Guyton, Arthur C., Blood Pressure Control Special Role of the Kidneys and Body Fluids, Science, vol. 252, Jun. 1991, 1813-1816.

Hafkenschiel, Joseph H. et al, Primary Hypertension Survey of the Survival of Patients with Established Diastolic Hypertension After Ten Years of Medical and Surgical Treatment, The American Journal of Cardiology, vol. 16, Jul. 1965, 61-66.

Hafkenschiel, Joseph H. et al, The Surgical Treatment of Hypertension with Particular Reference to Andrenalectomy and Sympathectomy, Transactions. American College of Cardiology, vol. 5, Dec. 1955, pp. 107-112.

Hall, J.E. et al, Role of Sympathetic Nervous System and Neuropeptides in Obesity Hypertension, Brazilian Journal of Medical and Biological Research, 2000, 33:605-618.

Hall, John E., The Kidney, Hypertension, and Obesity, Hypertension. 2003;41:625-633.

Hall, Winthrop H. et al, Combined Embolization and Percutaneous Radiofrequency Ablation of a Solid Renal Tumor, American Journal of Roentgenology, 174, Jun. 2000, 1592-1594.

Hamm, Christian et al, Confluence, Issue eight, Apr. 2014.

Han, Young-Min et al, Renal Artery Embolization with Diluted Hot Contrast Medium: An Experimental Study, Journal of Vascular and Interventional Radiology, Jul. 2001;12(7):862-868.

Hansen, Jesper Melchoir et al, The Transplanted Human Kidney Does Not Achieve Functional Reinnervation, Clinical Science, (1994) 87, 13-20.

Heuer, George J., The Surgical Treatment of Essential Hypertension, Annals of Surgery, Oct. 1936, vol. 104, No. 3, 771-786.

Hinton, J. William, End Results of Thoracolumbar Sympathectomy for Advanced Essential Hypertension, The Bulletin, Apr. 1948, 239-252.

Holmer, Stephan et al, Role of Renal Nerves for the Expression of Renin in Adult Rat Kidney, The American Journal of Physiology, May 1994;266(5 Pt 2):F738-F745.

Hoobler, S.W. et al, The Effects of Splanchnicectomy on the Blood Pressure in Hypertension, Circulation Journal of The American Heart Association, vol. IV, Aug. 1951, 173-183.

Hoppe, Uta C. et al, Minimally Invasive System for Baroreflex Activation Therapy Chronically Lowers Blood Pressure with Pacemaker-like Safety Profile: Results from the Barostim Neo Ttrial, J Am Soc Hypertens. Jul.-Aug. 2012;6 (4):270-6.

Howard, James P. et al, Size of Blood Pressure Reduction from Renal Denervation: Insights from Meta-Analysis of Antihypertensive Drug Trials of 4121 Patients with Focus on Trial Design: the Converge Report, Heart 2013;0:1-9.

Howard, James P. et al, Unintentional Overestimation of an Expected Antihypertensive Effect in Drug and Device Trials: Mechanisms and Solutions, International Journal of Cardiology, vol. 172, Issue 1, Mar. 1, 2014, pp. 29-35.

Howell, Marcus H. et al, Tandem Stenting of Crossed Renal Arteries with Ostial Stenosis, Tex Heart Inst J. 2000; 27(2): 166-169.

Hoye, Neil A. et al, Endovascular Renal Denervation: A Novel Sympatholytic with Relevance to Chronic Kidney Disease, Clinical Kidney Journal Advance Access, (2013) 0: 1-8.

Huang, Shoei K. Stephen et al, Radiofrequency Catheter Ablation of Cardiac Arrhythmias, Basic Concepts and Clinical Applications, Wiley-Blackwell, Jun. 2000, 1-12.

(56) References Cited

OTHER PUBLICATIONS

Huang, Wann-Chu, Renal Denervation Prevents and Reverses Hyperinsulinemia-Induced Hypertension in Rats, Hypertension Journal of The American Heart Association, 1998;32:249-254.

Humpreys, Michael H., Renal Nerves and CKD: Is Renal Denervation the Answer?, Journal of The American Socity of Nephrology, 2012, 23: 1-3.

Irigoyen, M.C.C. et al, Baroreflex Control of Sympathetic Activity in Experimental Hypertension, Brazilian Journal of Medical and Biological Research, (1998) 31: 1213-1220.

Izzo, Jr, Joseph L. et al, The Sympathetic Nervous System and Baroreflexes in Hypertension and Hypotension, Current Hypertension Reports 1999, 3:254-263.

Jackman, Warren M. et al, Catheter Ablation of Arrhythmias, Proposed Anatomy and Catheter Ablation of Epicardial Posteroseptal and Left Posterior Accessory AV Pathways (Chapter 16), 2002, Futura Publishing Company, Inc., 321-343.

Moak, Jeffrey P. et al, Case Report: Pulmonary Vein Stenosis Following RF Ablation of Paroxysmal Atrial Fibrillation: Successful Treatment with Balloon Dilation, Journal of Interventional Cardiac Electrophysiology, Dec. 2000, 4, 4:621-631.

Mogil, Robert A. et al, Renal Innervation and Renin Activity in Salt Metabolism and Hypertension, American Journal of Physiology, vol. 216, No. 4, Apr. 1969, 693-697.

Morita, Hironobu et al, Neural Control of Urinary Sodium Excretion During Hypertonic NaCl Load in Conscious Rabbits: Role of Renal and Hepatic Nerves and Baroreceptors, Journal of the Autonomic Nervous System, 34 (1991) 157-170.

Morrissey, D.M. et al, Sympathectomy in the Treatment of Hypertension, The Lancet, Feb. 1953, 403-408.

Mortara, Andrea et al, Nonselective Beta-Adrenergic Blocking Agent, Carvedilol, Improves Arterial Baroflex Gain and Heart Rate Variability in Patients With Stable Chronic Heart Failure, Journal of the American College of Cardiology, vol. 36, No. 5, 2000, 1612-1618.

Moss, Jonathan, Interventional Radiology and Renal Denervation, Interventions, vol. 13, Issue 3, 2013.

Naghavi, Morteza et al, Thermography Basket Catheter: In Vivo Measurement of the Temperature of Atherosclerotic Plaques for Detection of Vulnerable Plaques, Catheterization and Cardiovascular Interventions 59:52-59 (2003).

Naidoo, N. et al, Thoracic Splanchnic Nerves: Implications for Splanchnic Denervation, Journal of Anatomy, Nov. 2001;199(Pt 5):585-590.

Nakagawa, A. et al, Selective Ablation of Porcine and Rabbit Liver Tissue Using Radiofrequency: Preclinical Study, European Surgical Research, 1999;31:371-379.

Nakagawa, Hiroshi et al, Inverse Relationship Between Electrode Size and Lesion Size During Radiofrequency Ablation With Active Electrode Cooling, Circulation. Aug. 4, 1998;98(5):458-465.

Nanni, Gregg S. et al, Control of Hypertension by Ethanol Renal Ablation, Radiology 148: 51-54, Jul. 1983.

Ndegwa, S., Catheter-Based Renal Denervation for Treatment-Resistant Hypertension [Issues in emerging health technologies issue 121]. Ottawa: Canadian Agency for Drugs and Technologies in Health; 2013.

Neutel, Joel M., Hypertension and Its Management: A Problem in Need of New Treatment Strategies, Journal of Renin-Angiotensin-Aldosterone System 2000 1: S10-S13.

Newcombe, C.P. et al, Sympathectomy for Hypertension, British Medical Journal, Jan. 1959, 142-144.

Ng, Fu Siong et al, Catheter Ablation of Atrial Fibrillation, Clinical Cardiology, 25, 384-394 (2002).

Norman, Roger A. et al, Role of the Renal Nerves in One-Kidney, One Clip Hypertension in Rats, Hypertension Journal of The American Heart Association, 1984;6:622-626.

Nozawa, Takashi et al, Effects of Long-Term Renal Sympathetic Denervation on Heart Failure After Myocardial Infarction in Rats, Heart Vessels (2002) 16:51-56.

O'Connor, Brian K. et al, Radiofrequency Ablation of a Posteroseptal Accessory Pathway Via the Middle Cardiac Vein in a Six-Year-Old Child, PACE, vol. 20, Oct. 1997, Part 1, 2504-2507.

O'Hagen, Kathleen P. et al, Renal Denervation Decreases Blood Pressure in DOCA-Treated Miniature Swine With Established Hypertension, American Journal of Hypertension, 1990; 3:62-64.

Oliveira, Vera L.L. et al, Renal Denervation Normalizes Pressure and Baroreceptor Reflex in High Renin Hypertension in Conscious Rats, Hypertension vol. 19, No. 2 Feb. 2, 1992, Supplement II, II-17-II-21.

Omran, Heyder et al, Echocardiographic Imaging of Coronary Sinus Diverticula and Middle Cardiac Veins in Patients with Preexcitation Syndrome: Impact—on Radiofrequency Catheter Ablation of Posteroseptal Accessory Pathways, PACE, vol. 18, Jun. 1995, 1236-1243.

Oparil, Suzanne et al, Renal Nerve Ablation: Emerging Role in Therapeutics; Blood Pressure, Oct. 2011, vol. 20, No. 5, pp. 253-255.

Oral, Hakan et al, Pulmonary Vein Isolation for Paroxysmal and Persistent Atrial Fibrillation, Circulation Journal of The American Heart Association, 2002;105:1077-1081.

Osborn, Jeffrey L. et al, Long-Term Increases in Renal Sympathetic Nerve Activity and Hypertension, Clinical and Experimental Pharmacology and Physiology (1997) 24,72-76.

Osborn, John W., The Sympathetic Nervous System and Long-Term Regulation of Arterial Pressure: What Are the Critical Questions?, Clinical and Experimental Pharmacology and Physiology (1997) 24, 68-71.

Ou, Baiqing et al, Baroreflex Sensitivity Predicts the Induction of Ventricular Arrhythmias by Cesium Chloride in Rabbits, Japanese Circulation Journal, 1999; 63: 783-788.

Oz, Mehmet, Pressure Relief, TIME Magazine, Monday, Jan. 9, 2012.

Page, Irvine H. et al, Mechanisms, Diagnosis and Treatment of Hypertension of Renal Vascular Origin, Annal of Internal Medicine, Aug. 1959, vol. 51, No. 2, 196-211.

Page, Irvine H. et al, Mechanisms, Diagnosis and Treatment of Hypertension of Renal Vascular Origin; Annals of Internal Medicine, Aug. 1959;51:196-211.

Page, Irvine H. et al, The Effect of Renal Denervation on the Level of Arterial Blood Pressure and Renal Function in Essential Hypertension, Journal of Clinical Investigation, 1935;14(1):27-30.

Page, Irvine H. et al, The Effects of Renal Denervation on Patients Suffering from Nephritis, J Clin Invest. 1935;14 (4):443-458.

Page, Irvine H., The Effect of Renal Efficiency of Lowering Arterial Blood Pressure in Cases of Essential Hypertension and Nephritis, Journal of Clinical Investigation, Nov. 1934; 13(6): 909-915.

Page, Max, Section of Surgery, Discussion on the Surgical Treatment of Hypertension, Proceedings of the Royal Society of Medicine, vol. XLI, Feb. 1948, 359-372.

Papademetriou, Vasilios, Hypertension and the Simplicity Renal Denervation System, Scientific Background, www.medtronic.com, 2011.

Pappone, Carlo et al, Circumferential Radiofrequency Ablation of Pulmonary Vein Ostia: A New Anatomic Approach for Curing Atrial Fibrillation, Circulation, Journal of The American Heart Association, 2000;102:2619-2628.

Parati, Gianfranco et al, The Human Sympathetic Nervous System: Its Relevance in Hypertension and Heart Failure, European Heart Journal (2012) 33, 1058-1066.

Parmar, Arundhati, Analyst: Medtronic Will Likely Acquire Another Hypertension Therapy Firm, Medcity News, Apr. 27, 2012; 3:06 p.m.; medcitynews.com.

Pavlovich, Christian P. et al, Percutaneous Radio Requency Ablation of Small Renal Tumors: Initial Results; The Journal of Urology, vol. 167, Jan. 10-15, 2002.

Peet, Max Minor, Hypertension and Its Surgical Treatment by Bilateral Supradiaphragmatic Splanchnicectomy, American Journal of Surgery, vol. 75, Issue 1, Jan. 1948, 48-68.

Perry, C. Bruce, Malignant Hypertension Cured by Unilateral Nephrectomy, British Heart Journal, Jul. 1945; 7(3): 139-142.

Persu, Alexandre et al, Renal Denervation: Ultima Ratio or Standard in Treatment-Resistant Hypertension, Hypertension Journal of The American Heart Association, Sep. 2012;60(3):596-606.

(56) References Cited

OTHER PUBLICATIONS

Peterson, Helen Hogh et al, Lesion Dimensions During Temperature-Controlled Radiofrequency Catheter Ablation of Left Ventricular Porcine Myocardium Impact of Ablation Site, Electrode Size, and Convective Cooling, Circulation Journal of The American Heart Association, 1999;99:319-325.
Plouin, Pierre-Francois et al, Blood Pressure Outcome of Angioplasty in Atherosclerotic Renal Artery Stenosis a Randomized Trial, Hypertension Journal of The American Heart Association, 1998;31:823-829.
Poutasse, Eugene F., Surgical Treatment of Renal Hypertension, American Journal of Surgery, vol. 107, Jan. 1964, 97-103.
Pugsley, M.K. et al, The Vascular System an Overview of Structure and Function, Journal of Pharmacological and Toxicological Methods 44 (2000) 333-340.
Putney, John Paul, Are Secondary Considerations Still "Secondary"?:An Examination of Objective Indicia of Nonobviousness Five Years After KSR, Intellectual Property Brief, vol. 4, Issue 2, Article 5, 2012, 45-59.
Ramsay, Lawrence E. et al, Blood Pressure Response to Percutaneous Transluminal Angioplasty for Renovascular Hypertension: An Overview of Published Series; British Medical Journal Mar. 3, 1990; 300(6724): 569-572.
Rippy, Marian K. et al, Catheter-Based Renal Sympathetic Denervation: Chronic Preclinical Evidence for Renal Artery Safety, Clin Res Cardiol (2011) 100:1095-1101.
Ritz, Eberhard, New Approaches to Pathogenesis and Management of Hypertension, Clin J Am Soc Nephrol 4: 1886-1891, 2009.
Zazgornik, Jan et al, Bilateral Nephrectomy: The Best, but Often Overlooked, Treatment for Refractory Hypertension in Hemodialysis Patients, AJH 1998; 11:1364-1370.
Jaff, Michael R. et al, Kidney Stenting Lowers Blood Pressure in Patients with Severe Hypertension; Catheterization and Cardiovascular Interventions; Published Online: Jun. 27, 2012 (DOI: 10.1002/ccd.24449); Print Issue Date: Sep. 2012. URL: http://onlinelibrary.wiley.com/doi/10.1002/ccd.24449/abstract.
Jain, Mudit K. et al, A Three-Dimensional Finite Element Model of Radiofrequency Ablation with Blood Flow and Its Experimental Validation, Annals of Biomedical Engineering, vol. 28, pp. 1075-1084, 2000.
Jais, Pierre et al, Efficacy and Safety of Septal and Left-Atrial Linear Ablation for Atrial Fibrillation, The American Journal of Cardiology, vol. 84 (9A), Nov. 1999, 139R-146R.
Janssen, Ben J.A. et al, Frequency-Dependent Modulation of Renal Blood Flow by Renal Nerve Activity in Conscious Rabbits, American Journal of Physiology, 1997, 273:R597-R608.
Janssen, Ben J.A. et al, Renal Nerves in Hypertension, Miner Electrolyte Metab 1989;15:74-82.
Jin, Yu et al, No Support for Renal Denervation in a Meta-Analysis, JACC vol. 62, No. 21, 2013 Correspondence Nov. 19/26, 2013:2029-30.
Kaltenbach, Benjamin et al, Renal Artery Stenosis After Renal Sympathetic Denervation, J Am Coll Cardiol. Dec. 25, 2012;60(25):2694-5.
Kaltenbach, Benjamin et al, Renal Sympathetic Denervation as Second-Line Therapy in Mild Resistant Hypertension: A Pilot Study, Catheterization and Cardiovascular Interventions 81:335-339 (2013).
Kamiya, Atsunori et al, Parallel Resetting of Arterial Baroreflex Control of Renal and Cardiac Sympathetic Nerve Activities During Upright Tilt in Rabbits, Am J Physiol Heart Circ Physiol 298: H1966-H1975, 2010.
Kandzari, David E. et al, Catheter-Based Renal Denervation for Resistant Hypertension: Rationale and Design of the Symplicity HTN-3 Trial, Clin. Cardiol. 35, 9, 528-535 (2012).
Kapural, Leonardo et al, Radiofrequency Ablation for Chronic Pain Control, Current Pain and Headache Reports 2001, 5:517-525.
Kassab, Salah et al, Renal Denervation Attenuates the Sodium Retention and Hypertension Associated with Obesity, Hypertension vol. 25, No. 4, Part 2 Apr. 1995.
Katholi, Richard E. et al, Decrease in Peripheral Sympathetic Nervous System Activity following Renal Denervation or Unclipping in the One-Kidney One-Clip Goldblatt Hypertensive Rat, The Journal of Clinical Investigation, Jan. 1982;69(1):55-62.
Katholi, Richard E. et al, Role of the Renal Nerves in the Pathogenesis of One-Kidney Renal Hypertension in the Rat, Hypertension. 1981;3:404-409.
Katholi, Richard E. et al, The Role of Renal Sympathetic Nerves in Hypertension: Has Percutaneous Renal Denervation Refocused Attention on Their Clinical Significance?; Progress in Cardiovascular Disease 52 (2009) 243-248.
Katritsis, Demosthenes et al, Recurrence of Left Atrium-Pulmonary Vein Conduction Following Successful Disconnection in Asymptomatic Patients, Europace (2004) 6, 425e432.
Killip III, Thomas, Oscillation of Blood Flow and Vascular Resistance During Mayer Waves, Circulation Research, vol. XI, Dec. 1962, 987-993.
Kingwell, Bronwyn A. et al, Assessment of Gain of Tachycardia and Bradycardia Responses of Cardiac Baroreflex, Am J Physiol Heart Circ Physiol 260:H1254-H1263, 1991.
Kirchheim, H. et al, Sympathetic Modulation of Renal Hemodynamics, Renin Release and Sodium Excretion, Klin Wochenschr (1989) 67: 858-864.
Klein, Ge et al, Endovascular Treatment of Renal Artery Aneurysms with Conventional Non-Detachable Microcoils and Guglielmi Detachable Coils, Br J Urol. Jun. 1997; 79(6):852-860.
Knight, Eric L. et al, Predictors of Decreased Renal Function in Patients with Heart Failure During Angiotensin-Converting Enzyme Inhibitor Therapy: Results from the Studies of Left Ventricular Dysfunction (SOLVD), American Heart Journal, vol. 138, No. 5, Part 1, Nov. 1999, 849-855.
Koepke, John P. et al, Functions of the Renal Nerves, The Physiologist, vol. 28, No. 1, Feb. 1985, 47-52.
Kompanowska-Jezierska, Elzbieta et al, Early Effects of Renal Denervation in the Anaesthetised Rat: Natriuresis and Increased Cortical Blood Flow, Journal of Physiology (2001), 531.2, pp. 527-534.
Krum, Henry et al, Catheter-Based Renal Sympathetic Denervation for Resistant Hypertension: A Multicentre Safety and Proof-of-Principle Cohort Study, www.thelancet.com vol. 373 Apr. 11, 2009 1275-1281.
Krum, Henry et al, Device-Based Antihypertensive Therapy: Therapeutic Modulation of the Autonomic Nervous System, Circulation. 2011;123:209-215.
La Grange, Ronald G. et al, Selective Stimulation of Renal Nerves in the Anesthetized Dog: Effect on Renin Release During Controlled Changes in Renal Hemodynamics, Circulation Research, Journal of The American Heart Association, 1973;33:704-712.
Labeit, Alexander Michael et al, Changes in the Prevalence, Treatment and Control of Hypertension in Germany? A Clinical-Epidemiological Study of 50.000 Primary Care Patients, PLOS ONE, Dec. 2012, vol. 7, Issue 12, e52229, 1-11.
Labonte, Sylvain, Numerical Model for Radio-Frequency Ablation of the Endocardium and its Experimental Validation, IEEE Transactions on Biomedical Engineering, vol. 41, No. 2. Feb. 1994, 108-115.
Lambert, Gavin W. et al, Health-Related Quality of Life After Renal Denervation in Patients With Treatment-Resistant Hypertension, Hypertension. 2012;60:1479-1484.
Lee, Sang Joon et al, Ultrasonic Energy in Endoscopic Surgery, Yonsei Medical Journal, vol. 40, No. 6, pp. 545-549, 1999.
Leertouwer, Trude C. et al, In-Vitro Validation, with Histology, of Intravascular Ultrasound in Renal Arteries, Journal of Hypertension 1999, vol. 17 No. 2, 271-277.
Leishman, A.W.D., Hypertension—Treated and Untreated, British Medical Journal, May 1959, 1361-1368.
Leonard, Bridget L. et al, Differential Regulation of the Oscillations in Sympathetic Nerve Activity and Renal Blood Flow Following Volume Expansion, Autonomic Neuroscience: Basic and Clinical 83 (2000) 19-28.
Levin, Stephen, Ardian: Succeeding Where Drugs Fail Treating Hypertension in the Cath Lab, In Vivo: The Business & Medicine Report, vol. 27, No. 10, Nov. 2009.

(56) References Cited

OTHER PUBLICATIONS

Litynski, Grzegorz S., Kurt Semm and the Fight against Skepticism: Endoscopic Hemostasis, Laparoscopic Appendectomy, and Semm's Impact on the "Laparoscopic Revolution", JSLS. Jul.-Sep. 1998; 2(3): 309-313.
Lu, David S.K. et al, Effect of Vessel Size on Creation of Hepatic Radiofrequency Lesions in Pigs: Assessment of the "Heat Sink" Effect, American Journal of Radiology, 178, Jan. 2002, 47-51.
Luscher, Thomas F. et al, Renal Nerve Ablation After Symplicity HTN-3: Confused at the Higher Level?; European Heart Journal, doi:10.1093/eurheartj/ehu195; May 14, 2014.
Lustgarten, Daniel L. et al, Cryothermal Ablation: Mechanism of Tissue Injury and Current Experience in the Treatment of Tachyarrhythmias, Progress in Cardiovascular Diseases, vol. 41, No. 6 May/Jun. 1999: pp. 481-498.
Mahfoud, Felix et al, Expert Consensus Document from the European Society of Cardiology on Catheter-Based Renal Denervation, European Heart Journal, Jul. 2013;34(28):2149-57.
Mancia, Giuseppe et al, Sympathetic Activation in the Pathogenesis of Hypertension and Progression of Organ Damage, Hypertension Journal of The American Heart Association, 1999, 34:724-728.
McGahan, John P. et al, History of Ablation, Tumor Ablation, 2005, pp. 3-16.
Medtronic, Inc., J.P. Morgan Healthcare Conference, Corrected Transcript, Jan. 13, 2014, Factset:Callstreet, www.callstreet.com.
Medtronic, Inc., Medtronic Announces U.S. Renal Denervation Pivotal Trial Fails to Meet Primary Efficacy Endpoint While Meeting Primary Safety Endpoint, www.medtronic.com, Jan. 9, 2014.
Medtronic, Inc., RDN Therapy with the Symplicity Renal Denervation System, Procedure Fact Sheet, www.medtronic.com, 2011.
Medtronic, Inc., Renal Denervation (RDN) Novel Catheter -based Treatment for Hypertension, Symplicity RDN System Common Q&A, 2011.
Medtronic, Inc., Scientific Basis Behind Renal Denervation for the Control of Hypertension, Dec. 2012, http://www.icimeeting.com/2012/images/stories/PDF/1448_Wilcox_I_Mon.pdf.
Mehdirad, Ali et al, Temperature Controlled RF Ablation in Canine Ventricle and Coronary Sinus using 7 Fr or 5 Fr Ablation Electrodes, PACE, vol. 21, Jan. 1998, Part II, 316-321.
Meredith, I T et al, Exercise Training Lowers Resting Renal But Not Cardiac Sympathetic Activity in Humans; Hypertension Journal of The American Heart Association, 1991;18:575-582.
Michaelis, Lawrence L. et al, Effects of Renal Denervation and Renin Depletion on the Renal Responses to Intravascular Volume Expansion, Ann Surg. Mar. 1972; 175(3): 424-430.
Millard, F.C. et al, Renal Embolization for Ablation of Function in Renal Failure and Hypertension, Postgraduate Medical Journal (1989) 65, 729-734.
Robbins, Ivan M. et al, Pulmonary Vein Stenosis After Catheter Ablation of Atrial Fibrillation, Circulation Journal of The American Heart Association, 1998;98:1769-1775.
Rocha-Singh, Krishna J., Catheter-Based Sympathetic Renal Denervation a Novel Strategy for the Treatment of Resistant Hypertension, Endovascular Today, Aug. 2009, 52-56.
Rocha-Singh, Krishna J., Renal Artery Denervation: A Brave New Frontier, Endovascular Today, Feb. 2012, 45-53.
Sanderson, John E. et al, Effect of B-Blockade on Baroreceptor and Autonomic Function in Heart Failure, Clinical Science (1999) 96, 137-146.
Santos, Mario et al, Renal Sympathetic Denervation in Resistant Hypertension, World J Cardiol Apr. 26, 2013; 5(4): 94-101.
Savard, Sebastien et al, Eligibility for Renal Denervation in Patients With Resistant Hypertension When Enthusiasm Meets Reality in Real-Life Patients, J Am Coll Cardiol. 2012;60(23):2422-2424.
Schauerte, Patrick et al, Catheter Ablation of Cardiac Autonomic Nerves for Prevention of Vagal Atrial Fibrillation, Circulation Journal of The American Heart Association, 2000, 102:2774-2780.
Schlaich, Markus P. et al, International Expert Consensus Statement: Percutaneous Transluminal Renal Denervation for the Treatment of Resistant Hypertension, Journal of the American College of Cardiology vol. 62, Issue 22, Dec. 3, 2013, pp. 2031-2045.
Schlaich, Markus P. et al, Renal Denervation as a Therapeutic Approach for Hypertension Novel Implications for an Old Concept, Hypertension Journal of The American Heart Association, 2009;54:1195-1201.
Schlaich, Markus P. et al, Renal Sympathetic-Nerve Ablation for Uncontrolled Hypertension, The New England Journal of Medicine, 2009; 361:932-934.
Schmieder, Roland E. et al, ESH Position Paper: Renal Denervation—An Iterventional Therapy of Resistant Hypertension, Journal of Hypertension, 2012, 30:837-841.
Schmieder, Roland E. et al, Updated EHS Position Paper on Interventional Therapy of Resistant Hypertension, EuroIntervention 2013; 9:R58-R66.
Sellers, Alfred M. et al, Adrenalectomy and Sympathectomy for Hypertension Ten Year Survival, Archives of Surgery, vol. 89, Nov. 1964, 880-886.
Sen, S.K., Some Observations on Decapsulation and Denervation of the Kidney, The British Journal of Urology, vol. 8, Issue 4, Dec. 1936, 319-328.
Shiraki, Iwao William, Correction of Renal Hypertension by Ligation of Stenotic Segmental Renal Artery, Urology, vol. IX, No. 3, Mar. 1977, 296-298.
Shonai, Takaharu et al, Renal Artery Aneurysm: Evaluation with Color Doppler Ultrasonography Before and After Percutaneous Transarterial Embolization, J Ultrasound Med 19:277-280, 2000.
Silver, Donald et al, Renovascular Hypertension From Renal Artery Compression by Congenital Bands, Annals of Surgery, Feb. 1976, 161-166.
Smith, Gardner W. et al, Surgical Results and the Diagnostic Evaluation of Renovascular Hypertension, Annals of Surgery, May 1968, 669-680.
Smith, Harold P. et al, Radiofrequency Neurolysis in a Clinical Model Neuropathological Correlation, J Neurosurg 55:246-253, 1981.
Smithwick, R.H., An Evaluation of the Surgical Treatment of Hypertension, The Bulletin, Nov. 1949; 25(11):698-716.
Smithwick, Reginald H. et al, Splanchnicectomy for Essential Hypertension, The Journal of the American Medical Association, vol. 152, No. 16, Aug. 1953, 1501-1504.
Solis-Herruzo, J.A. et al, Effects of Lumbar Sympathetic Block on Kidney Function in Cirrhotic Patients with Hepatorenal Syndrome, Journal of Hepatology, 1987; 5: 167-173.
Sowers, James R. et al, Diabetes, Hypertension, and Cardiovascular Disease: An Update, Hypertension Journal of The American Heart Association, 2001;37:1053-1059.
Stanley, James C., Surgical Treatment of Renovascular Hypertension, The American Journal of Surgery, vol. 174, Aug. 1997, 102-110.
Stella, Andrea et al, Effects of Reversible Renal Denervation on Haemodynamic and Excretory Functions of the Ipsilateral and Contralateral Kidney in the Cat, Journal of Hypertension 1986, 4: 181-188.
Stuart, Candace, Newest Frontier in Cardiac Care: Kidneys; Cardiovascular Business, Dec. 13, 2012.
Stuart, Mary, Masterminds of Ardian: An Interview With Inventors Mark Gelfand and Howard Levin, Windhover Information, Start-Up Jan. 1, 2011.
Sun, Yingxian et al, Risk of Coronary Stenosis with Venous Ablation for Epicardial Accessory Pathways, PACE, Apr. 2001, Part II, vol. 24, 605.
Swartz, John F. et al, Radiofrequency Endocardial Catheter Ablation of Accessory Atrioventricular Pathway Atrial Insertion Sites, Circulation Journal of The American Heart Association, 1993;87:487-499.
Teigen, Corey L. et al, Segmental Renal Artery Embolization for Treatment of Pediatric Renovascular Hypertension, Journal of Vascular and Interventional Radiology, 1992; 3:111-117.
Teixeira, Maria Do Carmo et al,1992; Role of the Peripheral Renin Profile in Predicting Blood Pressure Control After Bilateral Nephrectomy in Renal-Transplanted Patients, Nephrol Dial Transplant (1998) 13: 2092-2097.

(56) References Cited

OTHER PUBLICATIONS

Teo, W S et al, Radiofrequency Catheter Ablation of Accessory Pathways: The Initial Experience in Singapore, Singapore Medical Journal, 1994; vol. 35:36-40.

Thiebot, J. et al, Bilateral Nephrectomy by Embolization of the Renal Arteries: A Report on Five Cases (author's transl), Sem Hop. Apr. 8-15, 1980;56(13-14):670-5.

Thomas, George et al, Renal Denervation to Treat Resistant Hypertension: Guarded Optimism, Cleveland Clinic Journal of Medicine, vol. 79, No. 7, Jul. 2012, 501-510.

Thomas, Natalie A., Secondary Consideration in Nonobviousness Analysis: The Use of Objective Indicia Following KSR V. Teleflex, NYU Law Review, vol. 86, No. 6, Dec. 2011, 2070-2112.

Ting, Chih-Tai et al, Arterial Hemodynamics in Human Hypertension Effects of Angiotensin Converting Enzyme Inhibition, Hypertension Journal of The American Heart Association, 1993;22:839-846.

Uchida, Fumiya et al, Effect of Radiofrequency Catheter Ablation on Parasympathetic Denervation: A Comparison of Three Different Ablation Sites, PACE, vol. 21, Nov. 1998, Part II, 2517-2521.

Valente, John F. et al, Laparoscopic Renal Denervation for Intractable ADPKD-Related Pain, Nephrol Dial Transplant (2001) 16:160.

Villarreal, Daniel et al, Effects of Renal Denervation on Postprandial Sodium Excretion in Experimental Heart Failure, American Journal of Physiology, May 1994;266(5 Pt 2):R1599-R1604.

Vonend, Oliver et al, Secondary Rise in Blood Pressure After Renal Denervation, The Lancet, vol. 380, Issue 9843, p. 778, Aug. 25, 2012.

Vujaskovic, Z. et al, Effects of Intraoperative Hyperthermia on Canine Sciatic Nerve: Histopathologic and Morphometric Studies, Int. J. Hyperthermia, 1994, vol. 10, No. 6, 845-855.

Webb, R.L. et al, Functional Identification of the Central Projections of Afferent Renal Nerves, Clin. and Exper.—Theory and Practice, Ag(Suppl.I), 47-57 (1987).

Weinstock, Marta et al, Renal Denervation Prevents Sodium Retention and Hypertension in Salt-Sensitive Rabbits with Genetic Baroreflex Impairment, Clinical Science (1996) 90, 287-293.

Wilcox, Josiah N., Scientific Basis Behind Renal Denervation for the Control of Hypertension, Medtronic, Inc., Dec. 2012, 38 pages.

Winternitz, Sherry R. et al, Role of the Renal Sympathetic Nerves in the Development and Maintenance of Hypertension in the Spontaneously Hypertensive Rat, Journal of Clinical Investigation, vol. 66 Nov. 1980, 971-978.

Wolf-Maier, Katharina et al, Hypertension Treatment and Control in Five European Countries, Canada, and the United States, Hypertension. 2004;43:10-17.

Wyss, J.M. et al, Sensory Denervation of the Kidney Attenuates Renovascular Hypertension in the Rat, Am J Physiol Heart Circ Physiol 250:H82-H86, 1986.

Yamada, Yutaka et al, Age-Related Changes in Muscle Sympathetic Nerve Activity in Essential Hypertension, Hypertension Journal of The American Heart Association, 1989;13:870-877.

Young, Robert R. et al, Reversible Block of Nerve Conduction by Ultrasound Ultrasonic Blocking of Nerve Fibers, Arch Neurol. 1961;4(1):83-89.

\* cited by examiner

ASSEMBLY OF STAGGERED ABLATION ELEMENTS

RELATED APPLICATIONS

This application is based on and claims the benefit of U.S. Provisional Patent Application No. 61/260,978, filed on Nov. 13, 2009.

BACKGROUND OF THE INVENTION

The present invention relates generally to ablation devices and, more specifically, to an assembly of ablation elements arranged in a staggered configuration.

Hypertension is a major global public health concern. An estimated 30-40% of the adult population in the developed world suffers from this condition. Furthermore, its prevalence is expected to increase, especially in developing countries. Diagnosis and treatment of hypertension remain suboptimal, even in developed countries. Despite the availability of numerous safe and effective pharmacological therapies, including fixed-drug combinations, the percentage of patients achieving adequate blood-pressure control to guideline target values remains low. Much failure of the pharmacological strategy to attain adequate blood-pressure control is attributed to both physician inertia and patient non-compliance and non-adherence to a lifelong pharmacological therapy for a mainly asymptomatic disease. Thus, the development of new approaches for the management of hypertension is a priority. These considerations are especially relevant to patients with so-called resistant hypertension (i.e., those unable to achieve target blood-pressure values despite multiple drug therapies at the highest tolerated dose). Such patients are at high risk of major cardiovascular events.

Renal sympathetic efferent and afferent nerves, which lie within and immediately adjacent to the wall of the renal artery, are crucial for initiation and maintenance of systemic hypertension. Indeed, sympathetic nerve modulation as a therapeutic strategy in hypertension had been considered long before the advent of modern pharmacological therapies. Radical surgical methods for thoracic, abdominal, or pelvic sympathetic denervation had been successful in lowering blood pressure in patients with so-called malignant hypertension. However, these methods were associated with high perioperative morbidity and mortality and long-term complications, including bowel, bladder, and erectile dysfunction, in addition to severe postural hypotension. Renal denervation is the application of a chemical agent, or a surgical procedure, or the application of energy to partially or completely damage renal nerves to partially or completely block the renal nerve activities. Renal denervation reduces or completely block renal sympathetic nerve activity, increases renal blood flow (RBF), and decreases renal plasma norepinephrine (NE) content.

The objective of renal denervation is to neutralize the effect of renal sympathetic system which is involved in arterial hypertension. Device-based renal denervation may achieve such objective, but may produce possible complications of renal artery/vein stenosis. Thus, there is a need for a device that can perform renal denervation with reduced risk of renal artery/vein stenosis.

BRIEF SUMMARY OF THE INVENTION

Embodiments of the present invention are directed to an assembly of staggered ablation elements which are energized to produce ablation zones that span one or more open arc segments around the longitudinal axis, but the ablation zones of all the ablation elements projected longitudinally onto any lateral plane which is perpendicular to the longitudinal axis span a substantially closed loop around the longitudinal axis. The renal nerves are oriented generally longitudinally. Because the ablation zones do not form a closed loop, the risk of renal artery/vein stenosis is reduced or eliminated. On the other hand, because the ablation zones of all the ablation elements projected longitudinally onto any lateral plane span a substantially closed loop, a substantially complete renal denervation is achieved.

In accordance with an aspect of the present invention, an ablation catheter comprises an elongated catheter body extending longitudinally between a proximal end and a distal end along a longitudinal axis; and an ablation element assembly comprising a plurality of ablation elements connected to the catheter body, each ablation element to be energized to produce an ablation zone. The ablation elements are distributed in a staggered configuration such that the ablation zones of the ablation elements span one or more open arc segments around the longitudinal axis, and the ablation zones of all the ablation elements projected longitudinally onto any lateral plane which is perpendicular to the longitudinal axis span a substantially closed loop around the longitudinal axis.

In some embodiments, the ablation elements are discretely spaced from each other at least one of longitudinally or laterally, and at least two of the ablation elements are spaced from one another longitudinally. The ablation elements span one or more open arc segments around the longitudinal axis, but all the ablation elements projected longitudinally onto any lateral plane which is perpendicular to the longitudinal axis span a substantially closed loop around the longitudinal axis. The plurality of ablation elements are RF electrodes. The ablation elements are independently controlled to be energized in one of simultaneous manner, sequential manner, and arbitrary manner to produce the ablation zones.

In accordance with another aspect of the invention, an ablation catheter comprises an elongated catheter body extending longitudinally between a proximal end and a distal end along a longitudinal axis; and an electrode assembly comprising a plurality of ablation electrodes connected to the catheter body by resilient biasing members that bias the ablation electrodes outwardly away from the catheter body, each ablation electrode to be energized to produce an ablation zone. The electrode assembly is movable between a collapsed arrangement and an expanded arrangement, the resilient biasing members biasing the ablation electrodes outwardly away from the catheter body toward the expanded arrangement. The ablation electrodes are distributed in a staggered configuration such that the ablation zones of the ablation electrodes span one or more open arc segments around the longitudinal axis, and the ablation zones of all the ablation electrodes projected longitudinally onto any lateral plane which is perpendicular to the longitudinal axis span a substantially closed loop around the longitudinal axis.

In some embodiments, a plurality of temperature sensors thermally are coupled with the plurality of ablation electrodes to measure temperatures of the ablation electrodes. The catheter body includes a plurality of irrigation fluid channels near the plurality of ablation electrodes to direct irrigation fluid toward the ablation electrodes. Each one of the plurality of ablation electrodes has a corresponding resilient biasing member biasing the one ablation electrode outwardly away from the catheter body. At least some of the resilient biasing members are connected to the distal end of the catheter body. At least some of the resilient biasing members are connected to a circumferential surface of the catheter body proximal to the distal end. At least some of the ablation electrodes have a lateral dimension which is greater than a longitudinal dimension thereof. The ablation electrodes in the expanded arrangement contact surfaces to be ablated; and the ablation electrodes in the expanded arrangement span one or more open arc segments around the longitudinal axis, but all the ablation electrodes in the expanded arrangement projected longitudinally onto any lateral plane which is perpendicular to the longitudinal axis span a substantially closed loop around the longitudinal axis. The ablation electrodes are independently controlled to be energized in one of simultaneous manner, sequential manner, and arbitrary manner to produce the ablation zones In accordance with another aspect of the invention, an ablation catheter comprises an elongated catheter body extending longitudinally between a proximal end and a distal end along a longitudinal axis; and an electrode assembly connected to the catheter body, the electrode assembly comprising a plurality of spines. Each of the spines has a proximal end connected to the catheter body and a distal end. The distal ends of the spines are connected to a spine distal junction. Each spine includes an intermediate segment, a proximal stiffness change between the proximal end and the intermediate segment of the spine, and a distal stiffness change between the distal end and the intermediate segment of the spine. The spines include a plurality of ablation electrodes on the intermediate segments, each ablation electrode to be energized to produce an ablation zone. The electrode assembly is movable between a collapsed arrangement and an expanded arrangement with the intermediate segments of the spines in the expanded arrangement moving outwardly relative to the proximal ends and distal ends of the spines with respect to the collapsed arrangement. The ablation electrodes are distributed on the intermediate segments in a staggered configuration such that the ablation zones of the ablation electrodes span one or more open arc segments around the longitudinal axis, and the ablation zones of all the ablation electrodes projected longitudinally onto any lateral plane which is perpendicular to the longitudinal axis span a substantially closed loop around the longitudinal axis.

In some embodiments, each spine includes a proximal leg coupled between the intermediate segment and the proximal end of the spine, and a distal leg coupled between the intermediate segment and the distal end of the spine. The proximal leg has a lower stiffness than the intermediate segment and the distal leg has a lower stiffness than the intermediate segment. Each spine includes a proximal hinge coupled between the proximal leg and the intermediate segment and a distal hinge coupled between the distal leg and the intermediate segment. The proximal leg is smaller in cross-section than the intermediate segment and the distal leg is smaller in cross-section than the intermediate segment. A plurality of temperature sensors thermally coupled with the plurality of ablation electrodes to measure temperatures of the ablation electrodes. The spines include a plurality of irrigation fluid channels near the plurality of ablation electrodes to direct irrigation fluid toward the ablation electrodes. At least some of the ablation electrodes have a lateral dimension which is greater than a longitudinal dimension thereof. The ablation electrodes in the expanded arrangement contact surfaces to be ablated; and the ablation electrodes in the expanded arrangement span one or more open arc segments around the longitudinal axis, but all the ablation electrodes in the expanded arrangement projected longitudinally onto any lateral plane which is perpendicular to the longitudinal axis span a substantially closed loop around the longitudinal axis. At least one of the spines includes a shape memory material that biases the spine toward the expanded arrangement.

These and other features and advantages of the present invention will become apparent to those of ordinary skill in the art in view of the following detailed description of the specific embodiments.

DETAILED DESCRIPTION OF THE INVENTION

Figure 1:
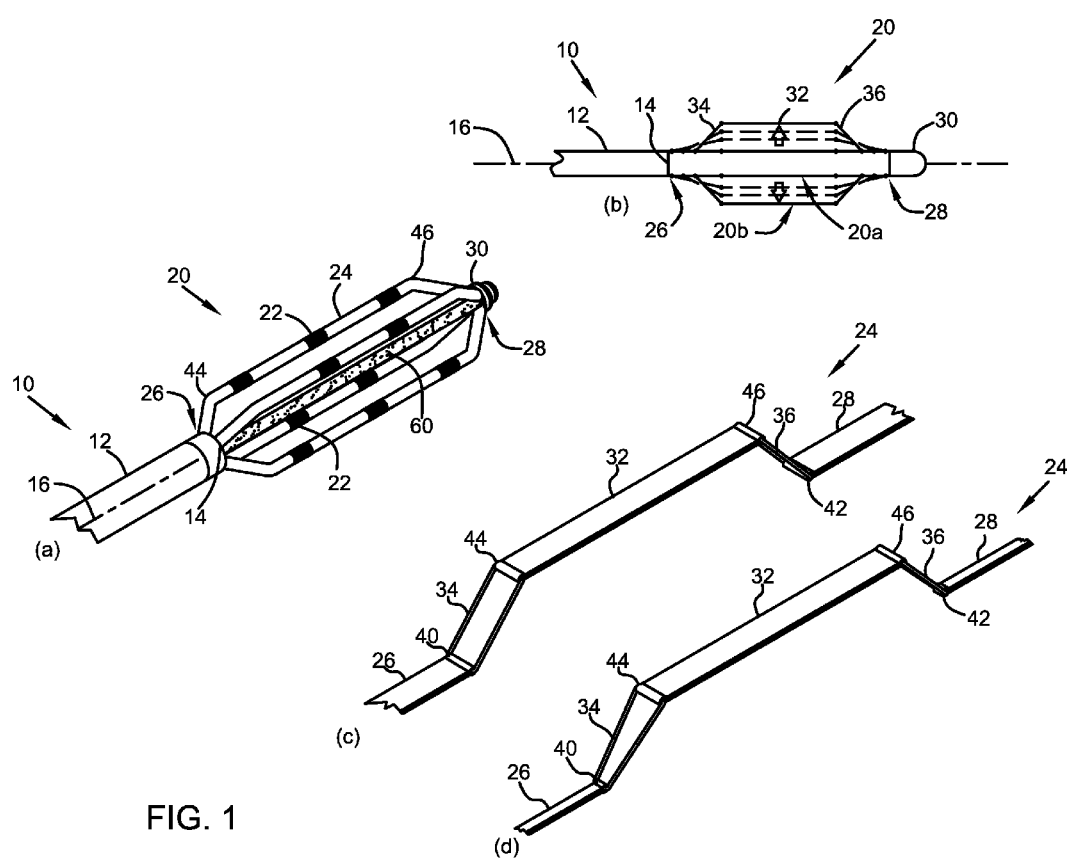
FIG. 1 illustrates an assembly of staggered ablation elements for a catheter according to an embodiment of the present invention.

In the following detailed description of the invention, reference is made to the accompanying drawings which form a part of the disclosure, and in which are shown by way of illustration, and not of limitation, exemplary embodiments by which the invention may be practiced. In the drawings, like numerals describe substantially similar components throughout the several views. Further, it should be noted that while the detailed description provides various exemplary embodiments, as described below and as illustrated in the drawings, the present invention is not limited to the embodiments described and illustrated herein, but can extend to other embodiments, as would be known or as would become known to those skilled in the art. Reference in the specification to "one embodiment," "this embodiment," or "these embodiments" means that a particular feature, structure, or characteristic described in connection with the embodiment is included in at least one embodiment of the invention, and the appearances of these phrases in various places in the specification are not necessarily all referring to the same embodiment. Additionally, in the following detailed description, numerous specific details are set forth in order to provide a thorough understanding of the present invention. However, it will be apparent to one of ordinary skill in the art that these specific details may not all be needed to practice the present invention. In other circumstances, well-known structures, materials, circuits, processes and interfaces have not been described in detail, and/or may be illustrated in block diagram form, so as to not unnecessarily obscure the present invention.

In the following description, relative orientation and placement terminology, such as the terms horizontal, vertical, left, right, top and bottom, is used. It will be appreciated that these terms refer to relative directions and placement in a two dimensional layout with respect to a given orientation of the layout. For a different orientation of the layout, different relative orientation and placement terms may be used to describe the same objects or operations.

Exemplary embodiments of the invention, as will be described in greater detail below, provide assemblies of staggered ablation elements that are particularly suitable for renal denervation with a reduced risk of stenosis.

FIG. 1 illustrates an assembly of staggered ablation elements for a catheter according to an embodiment of the present invention. In the perspective view of FIG. 1a, an ablation catheter 10 includes an elongated catheter body 12 extending longitudinally between a proximal end (not shown) and a distal end 14 along a longitudinal axis 16. An ablation element assembly 20 includes a plurality of ablation elements 22 connected to the catheter body 12. The ablation elements 22 are discretely spaced from each other longitudinally and/or laterally, and at least two of the ablation elements 22 are spaced from one another longitudinally.

In this embodiment, the ablation elements 22 are electrodes such as RF electrodes. The ablation electrode assembly 20 is connected to the distal end 14 of the catheter body 12. As seen in FIGS. 1a-1d, the electrode assembly 20 includes a plurality of spines 24, which may be oriented generally longitudinally. Each spine 24 has a proximal end 26 connected to the catheter body 12 and a distal end 28. The distal ends 28 of the spines 24 are connected to a spine distal junction 30. Each spine 24 includes an intermediate segment 32, a proximal stiffness change between the proximal end 26 and the intermediate segment 32 of the spine 24, and a distal stiffness change between the distal end 28 and the intermediate segment 32 of the spine 24. The spines 24 include a plurality of ablation electrodes 22 on the intermediate segments 32.

As shown in FIG. 1b, the electrode assembly 20 is movable between a collapsed arrangement 20a and an expanded arrangement 20b with the intermediate segments 32 of the spines 24 in the expanded arrangement 20b moving outwardly relative to the proximal ends 26 and distal ends 28 of the spines 24 with respect to the collapsed arrangement 20a.

Each spine 24 includes a proximal leg 34 coupled between the intermediate segment 32 and the proximal end 26 of the spine 24, and a distal leg 36 coupled between the intermediate segment 32 and the distal end 28 of the spine 24. Each spine 24 includes a proximal hinge 44 coupled between the proximal leg 34 and the intermediate segment 32 and a distal hinge 46 coupled between the distal leg 36 and the intermediate segment 32. The hinges 44, 46 represent the stiffness changes in this embodiment to facilitate movement of the intermediate segments 32 of the spines 24 between the collapsed arrangement 20a and the expanded arrangement 20b. In addition, each spine 24 may further include a proximal end hinge 40 coupled between the proximal leg 34 and the proximal end 26 and a distal end hinge 42 coupled between the distal leg 36 and the distal end 28 to further facilitate movement of the intermediate segments 32 of the spines 24 between the collapsed arrangement 20a and the expanded arrangement 20b.

In use, the catheter 10 with the electrode assembly 20 is inserted into a blood vessel or the like in the collapsed arrangement 20a (inside a guiding sheath or the like) and deployed into the expanded arrangement 20b. To allow blood flow in the blood vessel across the electrode assembly 20 and reduce or avoid obstruction, the spine 24 in FIG. 1c has narrow intermediate segment 32, proximal leg 34, and distal leg 36. In FIG. 1d, the intermediate segment 32 is wider while the proximal leg 34 and distal leg 36 are tapered so as to be smaller in cross-section than the intermediate segment 32, thereby reducing obstruction. Furthermore, the electrode assembly 20 preferably has no sharp corners or edges but has rounded corners and edges to facilitate easier and smoother movement within the blood vessel.

The ablation electrodes 22 in the expanded arrangement 20b contact surfaces to be ablated to ablate tissue and/or denervate nerves. To ensure surface contact for the ablation electrodes 22, the intermediate segments 32 preferably have sufficient stiffness to avoid or minimize bending in the expanded arrangement 20b. The electrode assembly 20 moves from the collapsed arrangement 20a to the expanded arrangement 20b by any suitable mechanism. In one example, any or all of the proximal leg 34, the distal leg 36, the proximal end hinge 40, and the distal end hinge 42 of the spine 24 may be resiliently biased (e.g., with a spring or a memory material) to move the electrode assembly 20 toward the expanded arrangement 20b. In another example, the longitudinal rod 60 in the center of the electrode assembly 20 is connected to the spine distal junction 30, and can be used to pull the spine distal junction 30 toward the distal end 14 of the catheter body 12 to move the electrode assembly 20 toward the expanded arrangement 20b.

Figure 2:
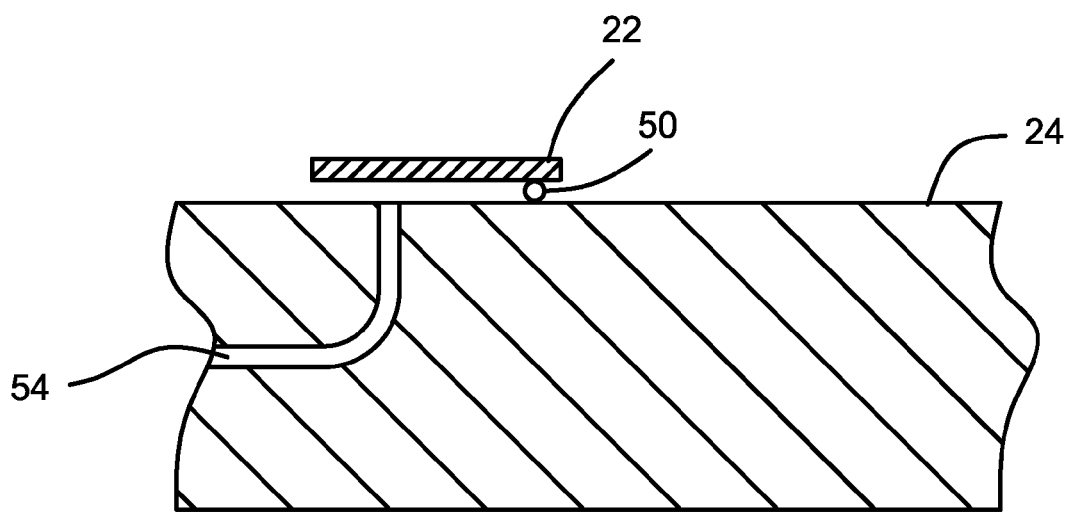
FIG. 2 is a cross-sectional view of a spine illustrating an example of a temperature sensor and an irrigation fluid channel.

A plurality of temperature sensors 50 are thermally coupled with the plurality of ablation electrodes 22 to measure temperatures of the ablation electrodes. FIG. 2 is a cross-sectional view of the spine 24 illustrating an example of a temperature sensor 50 disposed adjacent the electrode 22 supported on the spine 24. In addition, the spines 24 may include a plurality of irrigation fluid channels 54 near the plurality of ablation electrodes 22 to direct irrigation fluid toward the ablation electrodes 22, as seen in FIG. 2.

Figure 3:
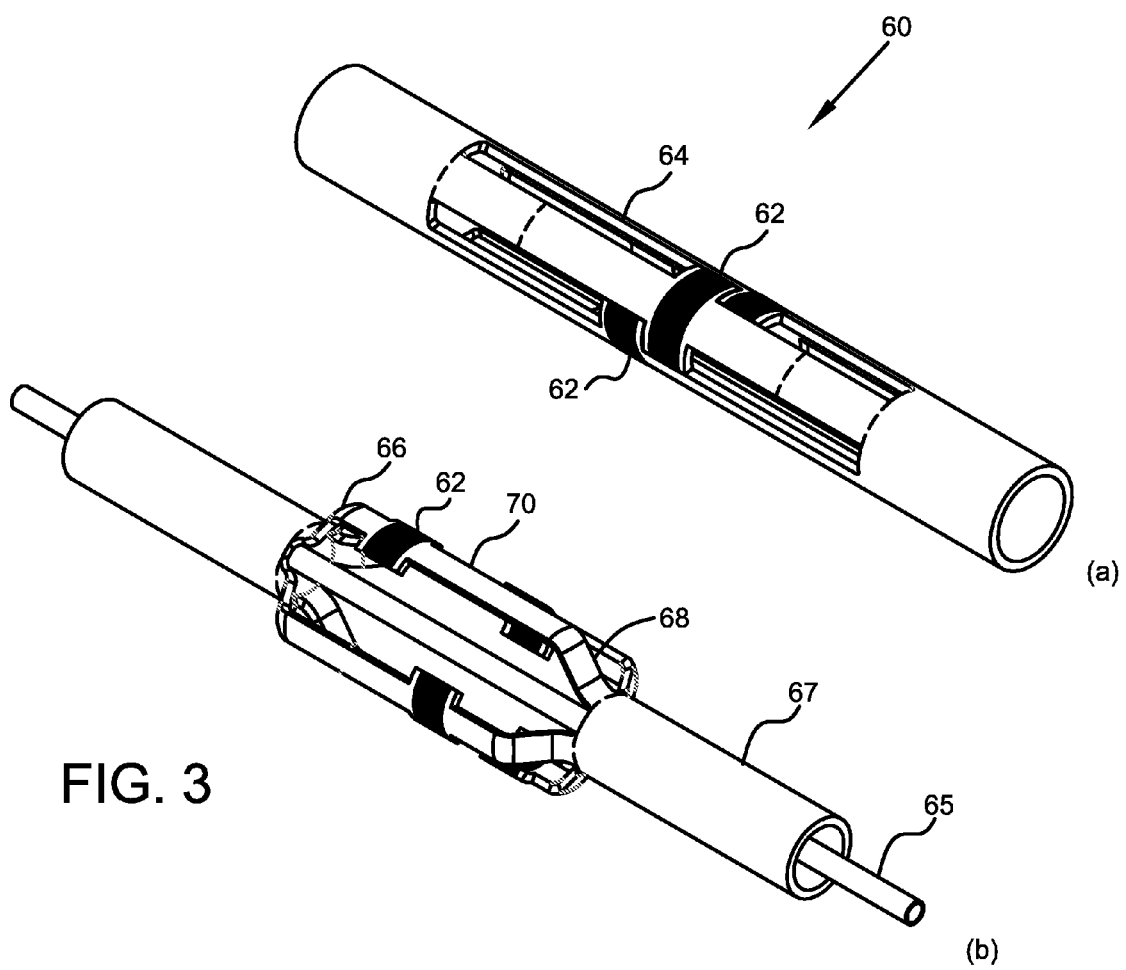
FIG. 3 illustrates an assembly of staggered ablation elements for a catheter according to another embodiment of the present invention.

FIG. 3 illustrates an assembly of staggered ablation elements for a catheter according to another embodiment of the present invention. FIG. 3a shows the electrode assembly 60 in a collapsed arrangement and FIG. 3b shows the electrode assembly 60 in an expanded arrangement. The electrode assembly 60 may be connected to the distal end of a catheter body or may be disposed proximally from the distal end of the catheter body.

The electrode assembly 60 of FIG. 3 differs from the electrode assembly 20 of FIG. 1 in several respects. First, the ablation electrodes 62 each have a lateral dimension which is greater than a longitudinal dimension thereof. The lateral dimension of the electrode 62 is greater than the lateral dimension of the spine 64 that supports the electrode 62. Each spine 64 has a proximal leg 66, a distal leg 68, and an intermediate segment 70. Each electrode 62 has the shape of a circumferential arch that produces an ablation zone that is oriented laterally with respect to the longitudinal axis. Such an ablation zone is more efficient and effective for denervating renal nerves that are oriented generally longitudinally.

Unlike the electrode assembly 20 of FIG. 1, the electrode assembly 60 of FIG. 3 does not include hinges on the spines. Instead, the spines 64 are configured to facilitate movement of the electrode assembly 60 from the collapsed arrangement to the expanded arrangement. For example, the proximal leg 66 has a lower stiffness than the intermediate segment 70 and the distal leg 68 has a lower stiffness than the intermediate segment 70. As a result, the proximal leg 66 and the distal leg 68 will bend or deform under a force that moves the electrode assembly 60 to the expanded arrangement. That force may be produced by at least one of the spines 64 made of a shape memory material (e.g., Nitinol). A longitudinal rod 65 in the center of the electrode assembly 60 may be connected to the spine distal junction 67, and can be used to pull the spine distal junction 67 in the proximal direction to move the electrode assembly 60 toward the expanded arrangement.

Figure 4:
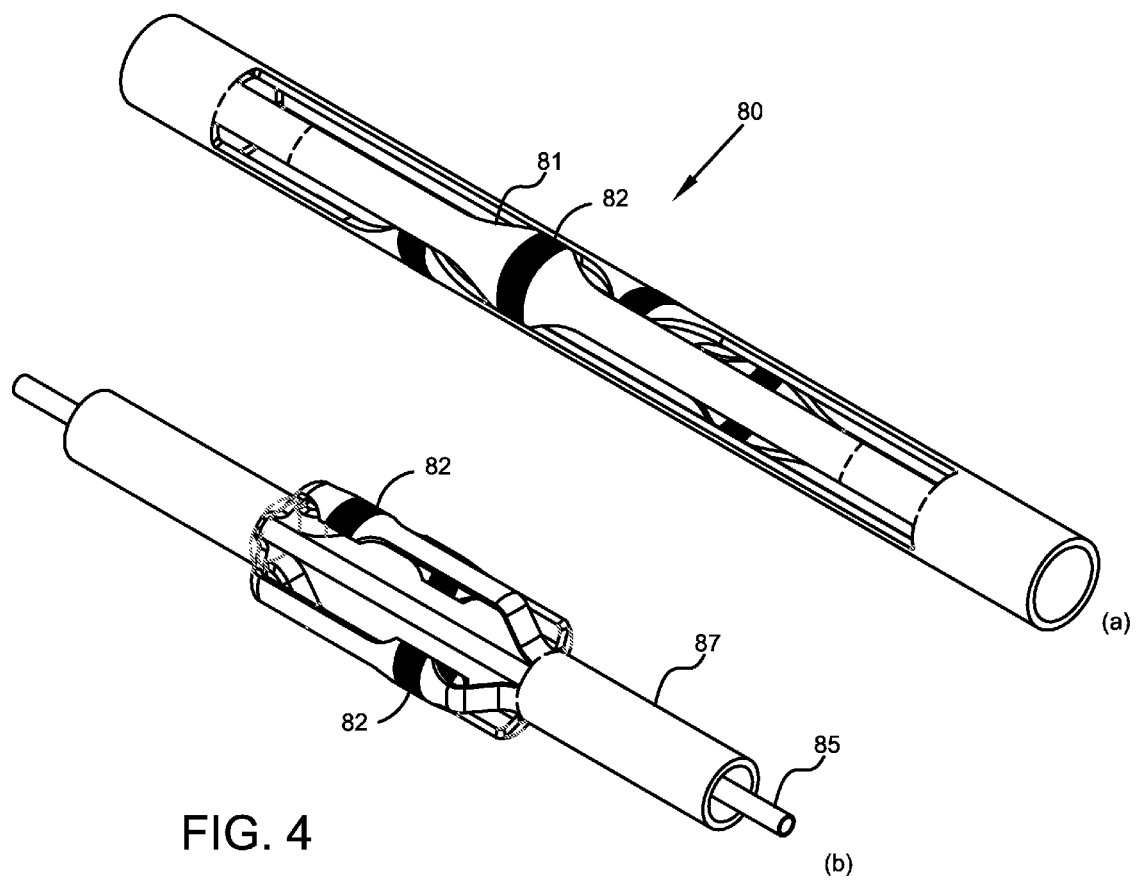
FIG. 4 illustrates an assembly of staggered ablation elements for a catheter according to another embodiment of the present invention.

FIG. 4 illustrates an assembly of staggered ablation elements for a catheter according to another embodiment of the present invention. FIG. 4a shows the electrode assembly 80 in a collapsed arrangement and FIG. 4b shows the electrode assembly 80 in an expanded arrangement. The electrode assembly 80 of FIG. 4 differs from the electrode assembly 60 of FIG. 3 in one respect. Tapered/rounded corners 81 replace sharp corners to facilitate easier and smoother movement of the electrode assembly within the blood vessel. A longitudinal rod 85 in the center of the electrode assembly 80 may be connected to the spine distal junction 87, and can be used to pull the spine distal junction 87 in the proximal direction to move the electrode assembly 80 toward the expanded arrangement.

Figure 5:
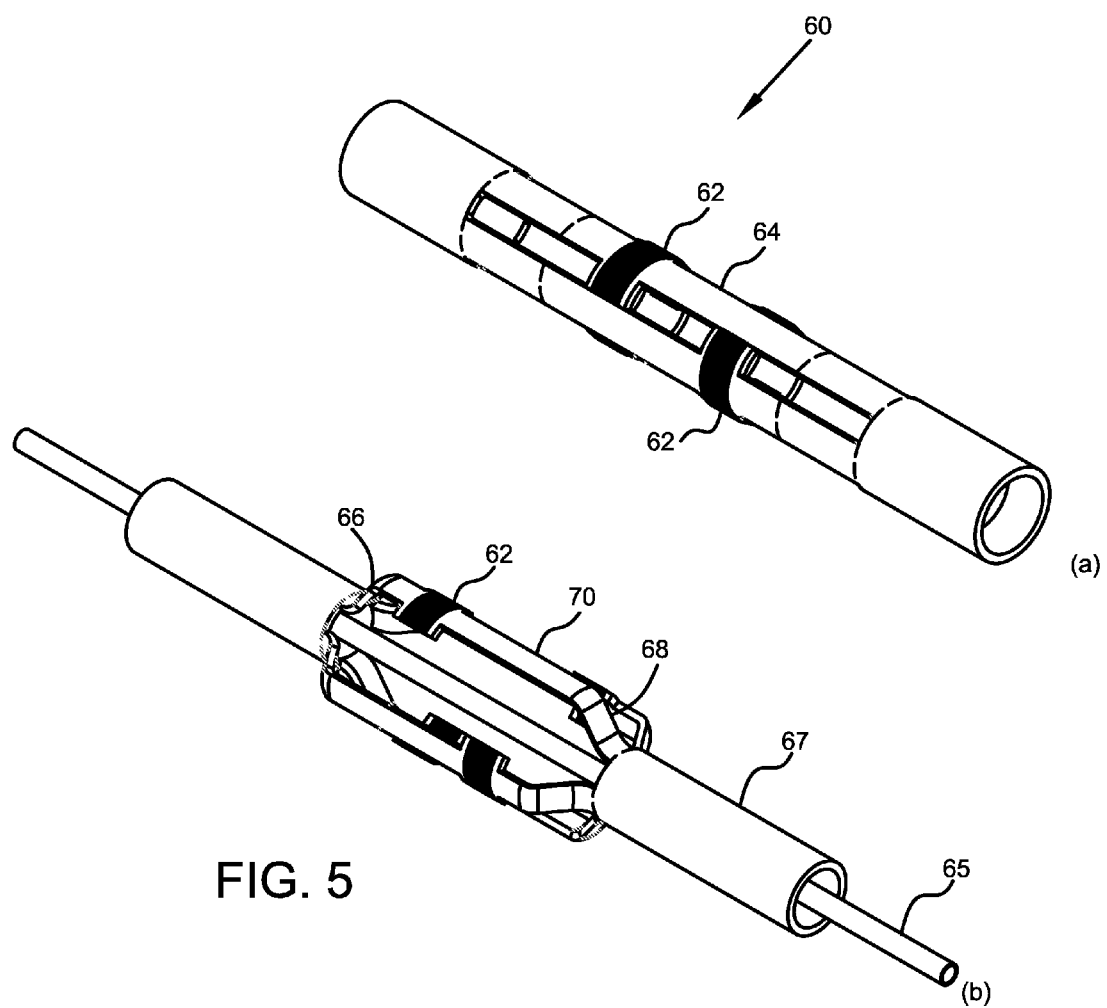
FIG. 5 illustrates an assembly of staggered ablation elements for a catheter according to another embodiment of the present invention.

The electrode assembly 60 of FIG. 5 is similar to the electrode assembly 60 of FIG. 3. They differ only in the arrangement of the ablation electrodes 62. In FIG. 3, the ablation electrodes 62 are staggered in a spiral manner in the longitudinal direction. In FIG. 5, the ablation electrodes 62 are arranged in nearly opposite pairs. These examples illustrate a few of the many different ways to arrange the staggered ablation electrodes 62 to form the electrode assemblies 60.

Figure 6:
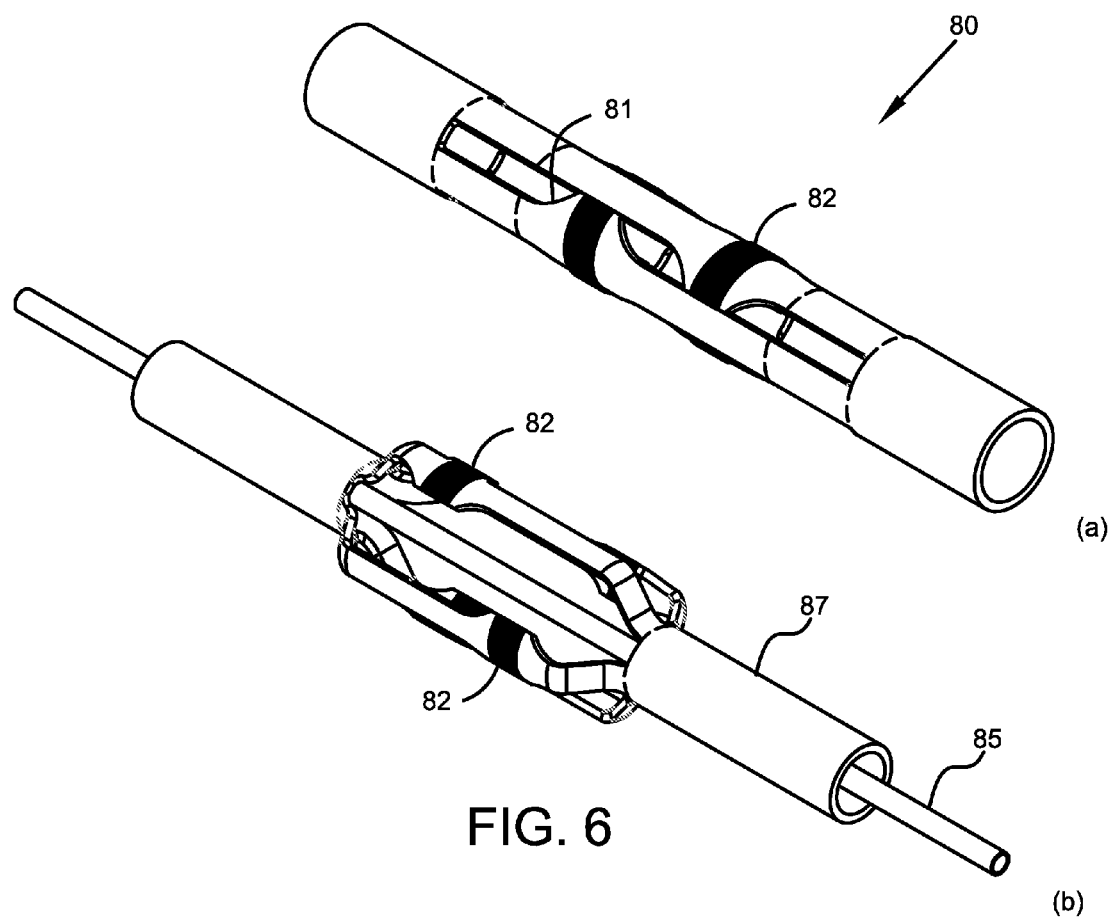
FIG. 6 illustrates an assembly of staggered ablation elements for a catheter according to another embodiment of the present invention.

The electrode assembly 80 of FIG. 6 is similar to the electrode assembly 80 of FIG. 4. They differ only in the arrangement of the ablation electrodes 82. In FIG. 4, the ablation electrodes 82 are staggered in a spiral manner in the longitudinal direction. In FIG. 6, the ablation electrodes 82 are arranged in nearly opposite pairs. These examples illustrate a few of the many different ways to arrange the staggered ablation electrodes 82 to form the electrode assemblies 80.

Figure 7:
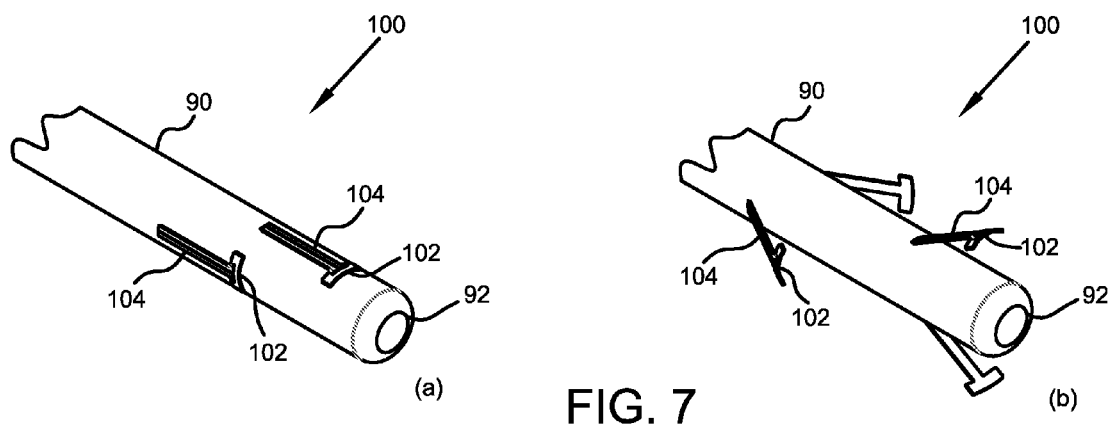
FIG. 7 illustrates an assembly of staggered ablation elements for a catheter according to another embodiment of the present invention.

FIG. 7 illustrates an assembly of staggered ablation elements for a catheter according to another embodiment of the present invention. A catheter body 90 with a distal end 92 is shown. FIG. 7a shows the electrode assembly 100 in a collapsed arrangement and FIG. 7b shows the electrode assembly 100 in an expanded arrangement. A plurality of ablation electrodes 102 are connected to the circumferential surface of the catheter body 90 proximally with respect to the distal end 92. The ablation electrodes 102 rest against the circumferential surface of the catheter body 90 in the collapsed arrangement of FIG. 7a. A plurality of resilient biasing members 104 bias the ablation electrodes 102 toward the expanded arrangement of FIG. 7b. In the embodiment shown, each ablation electrode 102 has a corresponding resilient biasing member 104 biasing the one ablation electrode 102 outwardly away from the catheter body 90. The ablation electrodes 102 are circumferential arches each having a lateral dimension greater than a longitudinal dimension thereof.

Figure 8:
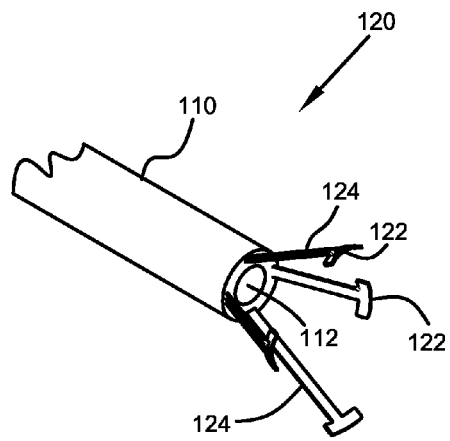
FIG. 8 illustrates an assembly of staggered ablation elements for a catheter according to another embodiment of the present invention.

FIG. 8 illustrates an assembly of staggered ablation elements for a catheter according to another embodiment of the present invention. A catheter body 110 with a distal end 112 is shown. The electrode assembly 120 includes a plurality of ablation electrodes 122 that are connected to the distal end 92 of the catheter body 90. A plurality of resilient biasing members 124 bias the ablation electrodes 122 outwardly toward the expanded arrangement as seen in FIG. 8.

Figure 9:
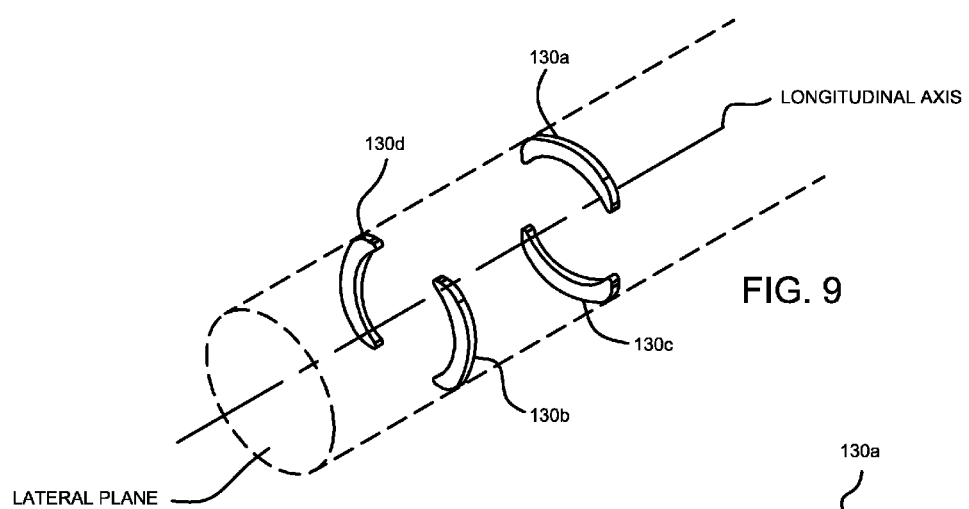
FIG. 9 illustrates the ablation zones of the ablation elements that span open arc segments around the longitudinal axis of the catheter.

FIG. 9 illustrates the ablation zones 130 of the ablation elements that span open arc segments around the longitudinal axis of the catheter. Each ablation element has a corresponding ablation zone (130a, 130b, 130c, . . . ). For each ablation element, the ablation zone is a region that is energized with sufficient energy to ablate tissue or denervate nerves within the ablation zone. The ablation zones 130 may be about the same in shape and size as the corresponding ablation elements. For RF electrodes or the like, the ablation zones are likely to be larger than the corresponding RF electrodes. The ablation elements are distributed in a staggered configuration such that the ablation zones 130 of the ablation elements span one or more open arc segments around the longitudinal axis.

Figure 10:
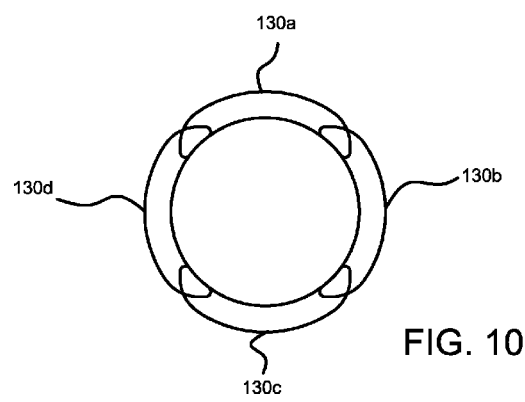
FIG. 10 illustrates the ablation zones of all the ablation elements that, when projected longitudinally onto any lateral plane which is perpendicular to the longitudinal axis, span a substantially closed loop around the longitudinal axis of the catheter.

FIG. 10 illustrates the ablation zones 130 of all the ablation elements that, when projected longitudinally onto any lateral plane which is perpendicular to the longitudinal axis, span a closed loop around the longitudinal axis of the catheter. In the embodiment illustrated by FIG. 10, the closed loop is completely closed. In other embodiments, the loop is substantially closed. The substantially closed loop has one or more open portions. The aggregate open portion of the substantially closed loop is about 30 percent or less of the substantially closed loop. An energy source supplies energy to the independently controlled ablation elements simultaneously or sequentially or in an arbitrary order to produce the ablation zones. In this way, tissue ablation or renal denervation or the like can be performed efficiently, effectively, and quickly, and in accordance with user selection.

In specific embodiments, the ablation electrodes in the expanded arrangement span one or more open arc segments around the longitudinal axis, but all the ablation electrodes in the expanded arrangement projected longitudinally onto any lateral plane which is perpendicular to the longitudinal axis span a substantially closed loop around the longitudinal axis. The substantially closed loop has one or more open portions. The aggregate open portion of the substantially closed loop is about 30 percent or less of the substantially closed loop.

Figure 11:
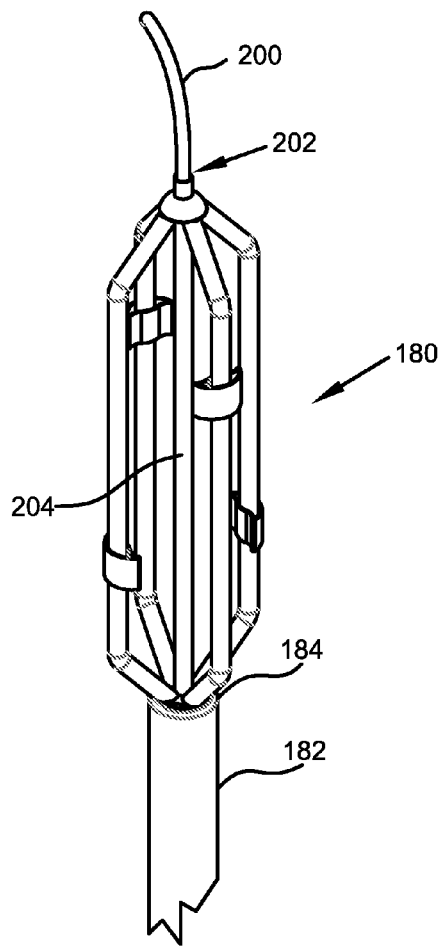
FIG. 11 illustrates an over-the-wire configuration for introducing the assembly of staggered ablation elements on a catheter to the surgical site by passing the guide wire through an internal lumen of the catheter.

FIG. 11 illustrates an over-the-wire configuration for introducing the assembly 180 of staggered ablation elements on a catheter to the surgical site by passing a guide wire 200 through an internal lumen of the catheter 182. The guide wire 200 extends through an opening 202 at the distal end of the assembly 180, and through a tube 204 that extends through the assembly 180 to the internal lumen of the catheter 182 from its distal end to its proximal end. The distal end of the assembly 180 is disposed distally of the distal end 184 of the catheter 182.

Figure 12:
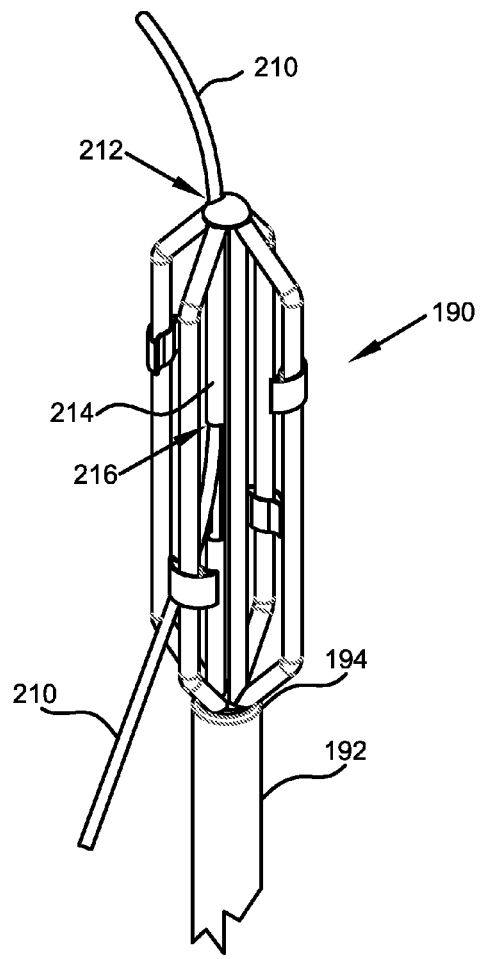
FIG. 12 illustrates an over-the-wire configuration for introducing the assembly of staggered ablation elements on a catheter to the surgical site by passing the guide wire through a hole provided at the distal end of the assembly of staggered ablation elements.

FIG. 12 illustrates an over-the-wire configuration for introducing the assembly 190 of staggered ablation elements on a catheter to the surgical site by passing a guide wire 210 through a distal opening 212 provided at the distal end of the assembly 190. The guide wire 210 extends through the distal opening 212 at the distal end of the assembly 190 and partially through a tube 214 with a cut-out or a side or intermediate opening 216, exiting via the cut-out or side/intermediate opening, and further extends externally of the catheter 192 toward the proximal end of the catheter 192. In FIG. 12, both the distal opening 212 and the intermediate opening 216 are disposed distally of the distal end 194 of the catheter 192.

In the description, numerous details are set forth for purposes of explanation in order to provide a thorough understanding of the present invention. However, it will be apparent to one skilled in the art that not all of these specific details are required in order to practice the present invention. Additionally, while specific embodiments have been illustrated and described in this specification, those of ordinary skill in the art appreciate that any arrangement that is calculated to achieve the same purpose may be substituted for the specific embodiments disclosed. This disclosure is intended to cover any and all adaptations or variations of the present invention, and it is to be understood that the terms used in the following claims should not be construed to limit the invention to the specific embodiments disclosed in the specification. Rather, the scope of the invention is to be determined entirely by the following claims, which are to be construed in accordance with the established doctrines of claim interpretation, along with the full range of equivalents to which such claims are entitled.

What is claimed is:

1. An ablation catheter comprising:
   an elongated catheter body extending longitudinally between a proximal end and a distal end along a longitudinal axis; and
   an electrode assembly connected to the catheter body, the electrode assembly comprising a plurality of spines, each of the plurality of spines having a proximal end connected to the catheter body and a distal end, the distal ends of the plurality of spines being connected to a spine distal junction, wherein each of the plurality of spines includes an intermediate segment, a proximal leg coupled between the intermediate segment and the proximal end and a distal leg coupled between the intermediate segment and the distal end, each of the plurality of spines further including a proximal hinge coupled between the proximal leg and the intermediate segment and a distal hinge coupled between the distal leg and the intermediate segment, a proximal stiffness change between the proximal end and the intermediate segment of each of the plurality of spines, and a distal stiffness change between the distal end and the intermediate segment of each of the plurality of spines, wherein each of the plurality of spines include a plurality of ablation electrodes on the intermediate segments, each of the plurality of ablation electrodes is configured to be energized to produce an ablation zone;
   wherein the electrode assembly is movable between a collapsed arrangement and an expanded arrangement with the intermediate segments of each of the plurality of spines in the expanded arrangement is configured to move outwardly relative to the proximal ends and distal ends of each of the plurality of spines with respect to the collapsed arrangement; and
   wherein the plurality of ablation electrodes are distributed on the intermediate segments in a staggered configuration such that the ablation zones of the plurality of ablation electrodes span one or more open arc segments around the longitudinal axis, and the ablation zones of all the plurality of ablation electrodes projected longitudinally onto any lateral plane which is perpendicular to the longitudinal axis span a substantially closed loop around the longitudinal axis.

2. The ablation catheter of claim 1,
   wherein the proximal leg of each of the plurality of spines has a lower stiffness than the intermediate sedment of each of the plurality of spines and the distal leg of each of the plurality of spines has a lower stiffness than the intermediate segment of each of the plurality of spines.

3. The ablation catheter of claim 1,
   wherein the proximal leg of each of the plurality of spines is smaller in cross-section than the intermediate segment of each of the plurality of spines and the distal leg of each of the plurality of spines is smaller in cross section than the intermediate segment of each of the plurality of spines.

4. The ablation catheter of claim 1, further comprising
   a plurality of temperature sensors thermally coupled with the plurality of ablation electrodes to measure temperatures of the plurality of ablation electrodes.

5. The ablation catheter of claim 1,
   wherein the plurality of spines include a plurality of irrigation fluid channels near the plurality of ablation electrodes to direct irrigation fluid toward the plurality of ablation electrodes.

6. The ablation catheter of claim 1,
   wherein at least some of the plurality of ablation electrodes have a lateral dimension which is greater than a longitudinal dimension thereof.

7. The ablation catheter of claim 1,
   wherein the plurality of ablation electrodes in the expanded arrangement are configured to contact surfaces to be ablated; and
   wherein the plurality of ablation electrodes in the expanded arrangement are configured to span one or more open arc segments around the longitudinal axis, and all the plurality of ablation electrodes in the expanded arrangement projected longitudinally onto any lateral plane which is perpendicular to the longitudinal axis are configured to span a substantially closed loop around the longitudinal axis.

8. The ablation catheter of claim 1,
   wherein at least one of the plurality of spines includes a shape memory material that biases the spine toward the expanded arrangement.

* * * * *